(12) United States Patent
Toth et al.

(10) Patent No.: US 11,872,043 B2
(45) Date of Patent: Jan. 16, 2024

(54) THIN FILM SUPPORT STRUCTURES

(71) Applicant: LifeLens Technologies, LLC, Ivyland, PA (US)

(72) Inventors: Landy Toth, Doylestown, PA (US); Robert S. Schwartz, Inver Grove Heights, MN (US)

(73) Assignee: LifeLens Technologies, LLC, Ivyland, PA (US)

( * ) Notice: Subject to any disclaimer, the term of this patent is extended or adjusted under 35 U.S.C. 154(b) by 1231 days.

(21) Appl. No.: 16/315,018

(22) PCT Filed: Jul. 10, 2017

(86) PCT No.: PCT/US2017/041291
§ 371 (c)(1),
(2) Date: Jan. 3, 2019

(87) PCT Pub. No.: WO2018/013447
PCT Pub. Date: Jan. 18, 2018

(65) Prior Publication Data
US 2019/0200890 A1   Jul. 4, 2019

Related U.S. Application Data

(60) Provisional application No. 62/362,313, filed on Jul. 14, 2016.

(51) Int. Cl.
*A61B 5/05* (2021.01)
*A61B 5/259* (2021.01)
(Continued)

(52) U.S. Cl.
CPC .............. *A61B 5/259* (2021.01); *A61B 5/145* (2013.01); *A61B 5/150022* (2013.01);
(Continued)

(58) Field of Classification Search
CPC .......... A61B 5/05; A61B 5/256; A61B 5/259; A61B 5/28; A61B 5/318; A61B 5/332;
(Continued)

(56) References Cited

U.S. PATENT DOCUMENTS

2006/0030767 A1 * 2/2006 Lang ...................... A61B 5/259
600/372
2008/0287770 A1 * 11/2008 Kurzweil ............. A61B 5/6804
600/388
(Continued)

FOREIGN PATENT DOCUMENTS

EP              17828225        3/2020
IN           201947001571       5/2021
WO  PCT/US2017/041291          9/2017

*Primary Examiner* — Joseph A Stoklosa
*Assistant Examiner* — Brian M Antiskay
(74) *Attorney, Agent, or Firm* — Ryan, Mason & Lewis, LLP

(57) ABSTRACT

A method includes forming a film, forming a first pattern of two or more vias at least partially through the film, attaching the film to a first support structure, the first support structure comprising an adhesive layer formed over a first carrier, wherein attaching the film to the first support structure comprises bonding a first surface of the film to the adhesive layer of the first support structure, wherein the film is stretchable in at least a first direction along the first surface, and wherein the first carrier maintains the first pattern of vias within a given threshold distortion following a given process conducted after attaching the film to the first support structure.

20 Claims, 21 Drawing Sheets

(51) Int. Cl.
| | |
|---|---|
| A61B 5/145 | (2006.01) |
| B32B 7/06 | (2019.01) |
| B32B 7/12 | (2006.01) |
| B32B 3/06 | (2006.01) |
| B32B 3/08 | (2006.01) |
| A61B 5/15 | (2006.01) |
| B32B 27/32 | (2006.01) |
| B32B 27/34 | (2006.01) |
| B32B 27/36 | (2006.01) |
| B32B 27/40 | (2006.01) |
| B32B 27/30 | (2006.01) |
| B32B 25/06 | (2006.01) |
| B32B 29/00 | (2006.01) |
| B32B 3/26 | (2006.01) |
| B32B 7/10 | (2006.01) |
| B32B 27/28 | (2006.01) |
| B32B 27/06 | (2006.01) |
| B32B 27/10 | (2006.01) |
| B32B 27/12 | (2006.01) |
| B32B 27/08 | (2006.01) |
| B32B 7/02 | (2019.01) |
| B32B 3/10 | (2006.01) |
| B32B 25/12 | (2006.01) |
| B32B 9/04 | (2006.01) |
| B32B 5/18 | (2006.01) |
| B32B 25/20 | (2006.01) |
| B32B 25/08 | (2006.01) |
| B32B 25/14 | (2006.01) |
| B32B 25/16 | (2006.01) |
| B32B 9/06 | (2006.01) |
| B32B 25/10 | (2006.01) |
| A61B 5/25 | (2021.01) |

(52) U.S. Cl.
CPC .. *A61B 5/150343* (2013.01); *A61B 5/150969* (2013.01); *A61B 5/25* (2021.01); *B32B 3/06* (2013.01); *B32B 3/08* (2013.01); *B32B 3/10* (2013.01); *B32B 3/26* (2013.01); *B32B 3/266* (2013.01); *B32B 5/18* (2013.01); *B32B 7/02* (2013.01); *B32B 7/06* (2013.01); *B32B 7/10* (2013.01); *B32B 7/12* (2013.01); *B32B 9/045* (2013.01); *B32B 9/047* (2013.01); *B32B 9/06* (2013.01); *B32B 25/06* (2013.01); *B32B 25/08* (2013.01); *B32B 25/10* (2013.01); *B32B 25/12* (2013.01); *B32B 25/14* (2013.01); *B32B 25/16* (2013.01); *B32B 25/20* (2013.01); *B32B 27/065* (2013.01); *B32B 27/08* (2013.01); *B32B 27/10* (2013.01); *B32B 27/12* (2013.01); *B32B 27/281* (2013.01); *B32B 27/285* (2013.01); *B32B 27/286* (2013.01); *B32B 27/306* (2013.01); *B32B 27/32* (2013.01); *B32B 27/34* (2013.01); *B32B 27/36* (2013.01); *B32B 27/365* (2013.01); *B32B 27/40* (2013.01); *B32B 29/007* (2013.01); *A61B 2562/028* (2013.01); *A61B 2562/12* (2013.01); *A61B 2562/125* (2013.01); *B32B 2250/02* (2013.01); *B32B 2250/03* (2013.01); *B32B 2250/44* (2013.01); *B32B 2255/10* (2013.01); *B32B 2255/205* (2013.01); *B32B 2255/26* (2013.01); *B32B 2255/28* (2013.01); *B32B 2266/12* (2016.11); *B32B 2270/00* (2013.01); *B32B 2307/202* (2013.01); *B32B 2307/308* (2013.01); *B32B 2307/51* (2013.01); *B32B 2307/546* (2013.01); *B32B 2307/706* (2013.01); *B32B 2307/732* (2013.01); *B32B 2437/00* (2013.01); *B32B 2437/02* (2013.01); *B32B 2439/46* (2013.01); *B32B 2457/00* (2013.01); *B32B 2535/00* (2013.01)

(58) Field of Classification Search
CPC ....... A61B 5/333; A61B 5/346; A61B 5/6831; A61B 5/6832; A61B 5/6833; A61B 5/68335; A61B 5/6879; A61B 5/688
USPC .................................. 600/372–395, 508–509
See application file for complete search history.

(56) References Cited

U.S. PATENT DOCUMENTS

| | | | |
|---|---|---|---|
| 2008/0288026 A1* | 11/2008 | Cross | A61B 5/6833 607/60 |
| 2010/0185077 A1* | 7/2010 | Chang | A61B 5/25 205/210 |
| 2013/0099358 A1 | 4/2013 | Elolampi et al. | |
| 2015/0082623 A1* | 3/2015 | Felix | A61B 5/25 29/825 |
| 2015/0094559 A1* | 4/2015 | Russell | A61B 5/0022 600/386 |
| 2015/0148646 A1* | 5/2015 | Park | H05K 1/115 174/262 |
| 2015/0197058 A1 | 7/2015 | Saha et al. | |
| 2015/0265173 A1* | 9/2015 | Datovech | A61B 5/282 600/393 |
| 2015/0351690 A1 | 12/2015 | Toth et al. | |
| 2015/0359485 A1* | 12/2015 | Berg | A61B 5/6804 600/388 |
| 2016/0089049 A1* | 3/2016 | Hung | A61B 5/333 600/391 |
| 2021/0393204 A1* | 12/2021 | Rogers | A61B 5/4266 |

* cited by examiner

THIN FILM SUPPORT STRUCTURES

CROSS-REFERENCE TO RELATED APPLICATIONS

The present application is a national stage of International Application PCT/US2017/041291, which claims the benefit of and priority to U.S. Provisional Application Ser. No. 62/362,313, filed on Jul. 14, 2016, the entire contents of which are incorporated by reference herein for all purposes.

TECHNICAL FIELD

The present disclosure relates to thin films and, more particularly, to devices including thin film support structures and manufacturing processes for producing thin film support structures.

BACKGROUND

In various applications areas, including but not limited to physiological monitoring and microelectronics, it is desired to miniaturize or reduce the size of devices. For example, in physiological monitoring, it may be important to measure physiologic parameters of subjects reliably, simply and without cables in an easy to use and unobtrusive manner. As another example, microelectronics used for tracking goods in a supply chain may utilize radio frequency identification (RFID) tags, near field communication (NFC) tags, readers for such RFID or NFC tags, etc. As devices continue to shrink in size, fabrication of the devices becomes more difficult.

SUMMARY

Described herein are thin film support structures and methods for forming the same that facilitate the use of thin films for stretchable, flexible and/or breathable devices in various application areas. Features and aspects of embodiments of the invention are set forth in the appended claims, in the following description, and in the annexed drawings in accordance with the present disclosure.

In one embodiment, a method comprises forming a film, forming a first pattern of two or more vias at least partially through the film, attaching the film to a first support structure, the first support structure comprising an adhesive layer formed over a first carrier, wherein attaching the film to the first support structure comprises bonding a first surface of the film to the adhesive layer of the first support structure, wherein the film is stretchable in at least a first direction along the first surface, and wherein the first carrier maintains the first pattern of vias within a given threshold distortion following a given process conducted after attaching the film to the first support structure.

In some embodiments, the given threshold distortion comprises distortion less than 1%, less than 0.25%, less than 0.1%, or less than 0.01%. The given threshold distortion may be distortion less than 10 micrometers (μm), less than 5 μm, or less than 1 μm. The given threshold distortion may be distortion in distance between centers of adjacent ones of the vias less than 10 μm, less than 5 μm, or less than 1 μm.

In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin, and the first carrier comprises one or more of biaxially-oriented polyethylene terephthalate (BoPET), polyethylene naphthalate (PEN), biaxially-oriented PEN (BoPEN), polyethylene terephthalate (PET), polycarbonate (PC)/acrylonitrile butadiene styrene (ABS), PC/acrylonitrile styrene (AS), polybutylene naphthalate (PBN), polyimide (PI), and polyphenylene sulfide (PPS).

In some embodiments, an elastic modulus of the first carrier is at least five times greater than an elastic modulus of the film, at least ten times greater than an elastic modulus of the film, at least fifty times greater than an elastic modulus of the film, at least one hundred times greater than an elastic modulus of the film, or at least five hundred times greater than an elastic modulus of the film.

In some embodiments, the given process comprises heating to a temperature greater than 100 degrees Celsius (° C.), greater than 120° C., greater than 140° C., greater than 160° C., or greater than 180° C. for at least one minute subsequent to attaching the film to the first support structure, for at least two minutes subsequent to attaching the film to the first support structure, for at least five minutes subsequent to attaching the film to the first support structure, or for at least ten minutes subsequent to attaching the film to the first support structure.

In some embodiments, the given process comprises cooling to a temperature less than 5° C., less than 0° C., less than −10° C., or less than −15° C. for at least five seconds subsequent to attaching the film to the first support structure, for at least thirty seconds subsequent to attaching the film to the first support structure, for at least one minute subsequent to attaching the film to the first support structure, or for at least two minutes subsequent to attaching the film to the first support structure.

In some embodiments, the method further comprises forming one or more microelectronic structures registered to one or more of the vias, the registration being within 1 millimeters (mm) of a preferred positioning, within 0.5 mm of a preferred positioning, within 0.25 mm of a preferred positioning, within 0.1 mm of a preferred positioning, within 0.05 mm of a preferred positioning, or within 0.025 mm of a preferred positioning.

In some embodiments, the method further comprises exposing the film to a chemical that at least partially solvates the film.

In some embodiments, the given process comprises pulling the film along a web after attaching the film to the first support structure or roll-to-roll or web based processing of the film after attaching the film to the first support structure.

In some embodiments, the method further comprises at least partially filling one or more of the vias with an electrically conducting material, with a thermally conducting material, or with an electrically and thermally conducting material.

In some embodiments, forming the film further comprises bonding a second surface of the film to a second carrier to form a second support structure, the second surface of the film being opposite the first surface of the film and attaching the film to the support structure comprises attaching the second support structure to the first support structure and removing the second carrier. In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin, and the second carrier comprises one or more of biaxially oriented polypropylene (BOPP), casting paper, polycarbonate, polyethylene, a print receptive substrate, a siliconized liner, a polyester liner, and a web-supporting material.

In some embodiments, the film has a thickness of 0.0025 to 1.0 mm.

In some embodiments, the film comprises a stretchable and breathable material. In some embodiments, the film comprises a stretchable, breathable, and elastically recoverable material.

In some embodiments, the method further comprises forming at least one split in the first carrier prior to attaching the film to the first support structure.

In some embodiments, the method further comprises curing or drying the adhesive layer prior to attaching the film to the first support structure. In some embodiments, the adhesive layer comprises one or more of a low tack gel adhesive, a crosslinked gel polymer, a pressure sensitive adhesive, and a low tack adhesive. In some embodiments, the adhesive layer comprises a friction lowering substance such that a thin residue remains on the film after removing the first support structure from the film, the friction lowering substance comprising one or more of a polymer resin, an oil, an excipient, a blooming agent, a silicone oil, and a wax.

In some embodiments, the method further comprises forming at least one functional feature over a second surface of the film, the second surface of the film being opposite the first surface of the film. In some embodiments, forming the at least one functional feature comprises forming the at least one functional feature aligned with at least one of the vias. In some embodiments, forming the at least one functional feature comprises forming the at least one functional feature registered to at least one of the vias. In some embodiments, the at least one functional feature comprises a gasket facilitating attachment of the film to another structure, the gasket being formed prior to attaching the film to the first support structure. In some embodiments, the at least one functional feature comprises an electrical feature, a capacitive element, a resistive element, a touch sensitive component, a flexible display element, a pixel, an analyte sensing element, a printed electrochemical sensor, a conductive element, a magnetic element, an inductive element, a contact, an electrode, an antenna, a touch sensitive element, or a light sensitive element.

In some embodiments, attaching the film to the first support structure comprises laminating the first surface of the film to the adhesive layer.

In some embodiments, at least one of the vias is formed completely through the film. In some embodiments, the method further comprises depositing an additional material on regions of the adhesive layer exposed by the at least one via formed completely through the film. In some embodiments, the additional material comprises a conductive material. In some embodiments, the conductive material comprises an electrically conductive material, a thermally conductive material, or an electrically and thermally conductive material. In some embodiments, the conductive material adheres more strongly to the film than to the adhesive layer. In some embodiments, the conductive material comprises an adhesive strength to the adhesive layer of less than 75 grams per inch (g/in), of less than 50 g/in, of less than 25 g/in, or of less than 10 g/in. In some embodiments, the additional material comprises a release coating. In some embodiments, the release coating comprises one or more of a siliconized release coating, a mold release medium, and a wax. In some embodiments, the additional material comprises a release coating and a conductive material formed over the release coating. In some embodiments, the conductive material adheres more strongly to the film than to the release coating. In some embodiments, the conductive material comprises an adhesive strength to the release coating of less than 75 g/in, of less than 50 g/in, of less than 25 g/in, or of less than 10 g/in.

In some embodiments, the method further comprises forming a priming surface over at least a portion of a second surface of the film, the second surface of the film being opposite the first surface of the film. In some embodiments, the priming surface comprises one or more of an organometallic self-assembled monolayer, a titanate, a zirconate, an aluminate, an organosilane, a silane, and a siloxane.

In some embodiments, the method further comprises forming at least one functional feature in at least one of the vias. In some embodiments, the at least one functional feature comprises a microelectronic structure comprising one or more layers. In some embodiments, at least one of the layers of the microelectronic structure has a thickness less than 50 μm. In some embodiments, the microelectronic structure has an equivalent bulk elastic modulus of less than 900 megapascals (MPa). In some embodiments, the microelectronic structure has an equivalent flexural modulus of less than 1 gigapascal (GPa). In some embodiments, a moisture vapor transfer rate (MVTR) in an area of the film proximate the microelectronic structure is greater than 50 grams per square meter per day (g/m$^2$/day).

In some embodiments, the method further comprises forming a first functional feature in a first one of the vias and forming at least a first functional layer over a second surface of the film opposite the first surface of the film, the first functional layer connecting to the first functional feature. In some embodiments, the method further comprises forming a second functional feature in a second one of the vias, the first functional layer connecting the first functional feature to the second functional feature. In some embodiments, the first functional layer comprises a patterned trace. In some embodiments, forming the first functional layer comprises depositing a conducting layer over a first portion of the second surface of the film and at least one of curing and drying the conducting layer to form one or more wrinkles therein, the conducting layer with wrinkles formed therein forming the patterned trace. In some embodiments, the wrinkles are formed with an amplitude oriented substantially in a direction perpendicular to the second surface of the film. In some embodiments, the wrinkles are formed with a wavelength propagating substantially along a length of the patterned trace. In some embodiments, the first functional feature comprises an electrical interconnect, a light emitting pixel, a flexible display, a light emitting temporary tattoo, a light emitting diode (LED), a flexible LED, an electrode, a reference electrode, an electrochemical sensor, a redox reactive sensing electrode, a light sensitive structure, a moisture sensitive structure, a pressure sensitive structure, or a magnetic structure.

In one embodiment, an apparatus comprises a first support structure comprising an adhesive layer formed over a first carrier and a film attached to the first support structure and comprising a first pattern of two or more vias formed at least partially therethrough, a first surface of the film being bonded to the adhesive layer of the first support structure, wherein the film is stretchable in at least a first direction along the first surface and wherein the first carrier comprises a material having a rigidity that maintains the first pattern of vias within a given threshold distortion following a given process conducted after the film is attached to the first support structure.

In some embodiments, the given threshold distortion comprises distortion less than 1%, less than 0.25%, less than 0.1%, or less than 0.01%. The given threshold distortion may be distortion less than 10 μm, less than 5 μm, or less than 1 μm. The given threshold distortion may be distortion in distance between centers of adjacent ones of the vias less than 10 μm, less than 5 μm, or less than 1 μm.

In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin, and the first carrier comprises one or more of biaxially-oriented polyethylene terephthalate (BoPET), polyethylene naphthalate (PEN), biaxially-oriented PEN (BoPEN), polyethylene terephthalate (PET), polycarbonate (PC)/acrylonitrile butadiene styrene (ABS), PC/acrylonitrile styrene (AS), polybutylene naphthalate (PBN), polyimide (PI), and polyphenylene sulfide (PPS).

In some embodiments, an elastic modulus of the first carrier is at least five times greater than an elastic modulus of the film, at least ten times greater than an elastic modulus of the film, at least fifty times greater than an elastic modulus of the film, at least one hundred times greater than an elastic modulus of the film, or at least five hundred times greater than an elastic modulus of the film.

In some embodiments, the given process comprises heating to a temperature greater than 100 degrees Celsius (° C.), greater than 120° C., greater than 140° C., greater than 160° C., or greater than 180° C. for at least one minute subsequent to attaching the film to the first support structure, for at least two minutes subsequent to attaching the film to the first support structure, for at least five minutes subsequent to attaching the film to the first support structure, or for at least ten minutes subsequent to attaching the film to the first support structure.

In some embodiments, the given process comprises cooling to a temperature less than 5° C., less than 0° C., less than −10° C., or less than −15° C. for at least five seconds subsequent to attaching the film to the first support structure, for at least thirty seconds subsequent to attaching the film to the first support structure, for at least one minute subsequent to attaching the film to the first support structure, or for at least two minutes subsequent to attaching the film to the first support structure.

In some embodiments, the apparatus further comprises one or more microelectronic structures registered to one or more of the vias, the registration being within 1 mm of a preferred positioning, within 0.5 mm of a preferred positioning, within 0.25 mm of a preferred positioning, within 0.1 mm of a preferred positioning, within 0.05 mm of a preferred positioning, or within 0.025 mm of a preferred positioning.

In some embodiments, the film is at least partially solvated by exposure to a chemical.

In some embodiments, the given process comprises pulling the film along a web after attaching the film to the first support structure or roll-to-roll or web based processing of the film after attaching the film to the first support structure.

In some embodiments, the apparatus further comprises an electrically conducting material at least partially filling one or more of the vias, a thermally conducting material at least partially filling one or more of the vias, or an electrically and thermally conducting material at least partially filling one or more of the vias.

In some embodiments, the film is part of a second support structure, the second support structure comprising a second carrier bonded to a second surface of the film, the second surface of the film being opposite the first surface of the film. In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin and the second carrier comprises one or more of biaxially oriented polypropylene (BOPP), casting paper, a print receptive substrate, a siliconized liner, a polyester liner, and a web-supporting material.

In some embodiments, the film has a thickness of 0.0025 to 1.0 mm.

In some embodiments, the film comprises a stretchable and breathable material. In some embodiments, the film comprises a stretchable, breathable, and elastically recoverable material.

In some embodiments, the first carrier has at least one split formed therein.

In some embodiments, the adhesive layer is dried or cured prior to attachment of the film to the first support structure. In some embodiments, the adhesive layer comprises one or more of a low tack gel adhesive, a crosslinked gel polymer, a pressure sensitive adhesive, and a low tack adhesive. In some embodiments, the adhesive layer comprises a friction lowering substance such that a thin residue remains on the film after removing the first support structure from the film, the friction lowering substance comprising one or more of a polymer resin, an oil, an excipient, a blooming agent, a silicone oil, and a wax.

In some embodiments, the apparatus further comprises at least one functional feature formed over a second surface of the film, the second surface of the film being opposite the first surface of the film. In some embodiments, the at least one functional feature is aligned with at least one of the vias. In some embodiments, the at least one functional feature is registered to at least one of the vias. In some embodiments, the at least one functional feature comprises a gasket facilitating attachment of the film to another structure. In some embodiments, the at least one functional feature comprises an electrical feature, a capacitive element, a resistive element, a touch sensitive component, a flexible display element, a pixel, an analyte sensing element, a printed electrochemical sensor, a touch sensitive element, or a light sensitive element.

In some embodiments, the first surface of the film is laminated to the adhesive layer. In some embodiments, at least one of the vias is formed completely through the film. In some embodiments, the apparatus further comprises an additional material deposited on regions of the adhesive layer exposed by the at least one via formed completely through the film. In some embodiments, the additional material comprises a conductive material. In some embodiments, the conductive material comprises an electrically conductive material, a thermally conductive material, or an electrically and thermally conductive material. In some embodiments, the conductive material adheres more strongly to the film than to the adhesive layer. In some embodiments, the conductive material comprises an adhesive strength to the adhesive layer of less than 75 g/in, less than 50 g/in, less than 25 g/in, or less than 10 g/in. In some embodiments, the additional material comprises a release coating. In some embodiments, the release coating comprises one or more of a siliconized release coating, a mold release medium, and a wax. In some embodiments, the additional material comprises a release coating and a conductive material formed over the release coating. In some embodiments, the conductive material adheres more strongly to the film than to the release coating. In some embodiments, the conductive material comprises an adhesive strength to the release coating of less than 75 g/in, less than 50 g/in, less than 25 g/in, or less than 10 g/in.

In some embodiments, the apparatus further comprises a priming surface formed over at least a portion of a second surface of the film, the second surface of the film being opposite the first surface of the film. In some embodiments, the priming surface comprises one or more of an organometallic self-assembled monolayer, a titanate, a zirconate, an aluminate, an organosilane, a silane, and a siloxane.

In some embodiments, the apparatus further comprises at least one functional feature formed in at least one of the vias. In some embodiments, the at least one functional feature comprises a microelectronic structure comprising one or more layers. In some embodiments, at least one of the layers of the microelectronic structure has a thickness less than 50 µm. In some embodiments, the microelectronic structure has an equivalent bulk elastic modulus of less than 900 megapascals (MPa). In some embodiments, the microelectronic structure has an equivalent flexural modulus of less than 1 gigapascal (GPa). In some embodiments, a moisture vapor transfer rate (MVTR) in an area of the film proximate the microelectronic structure is greater than 50 grams per square meter per day (g/m²/day).

In some embodiments, the apparatus further comprises a first functional feature formed in a first one of the vias and at least a first functional layer formed over a second surface of the film opposite the first surface of the film, the first functional layer connecting to the first functional feature. In some embodiments, the apparatus further comprises a second functional feature formed in a second one of the vias, the first functional layer connecting the first functional feature to the second functional feature. In some embodiments, the first functional layer comprises a patterned trace. In some embodiments, the patterned trace comprises a conducting layer that is at least one of cured and dried to form one or more wrinkles therein. In some embodiments, the wrinkles are formed with an amplitude oriented substantially in a direction perpendicular to the second surface of the film. In some embodiments, the wrinkles are formed with a wavelength propagating substantially along a length of the patterned trace. In some embodiments, the first functional feature comprises an electrical interconnect, a light emitting pixel, a flexible display, a light emitting temporary tattoo, a light emitting diode (LED), a flexible LED, an electrode, a reference electrode, an electrochemical sensor, a redox reactive sensing electrode, a light sensitive structure, a moisture sensitive structure, a pressure sensitive structure, or a magnetic structure.

In one embodiment, a patch comprises a first support structure comprising an adhesive layer formed over a first carrier, a film attached to the first support structure and comprising a first pattern of two or more vias formed at least partially therethrough, a first surface of the film being bonded to the adhesive layer of the first support structure, one or more microelectronic structures, the one or more microelectronic structures being at least one of: formed in at least one of the vias; and formed as a pattern on a second surface of the film, the second surface of the film being opposite the first surface of the film, a surface adhesive formed over at least a portion of the second surface of the film, and a liner attached to the surface adhesive, wherein the film is stretchable in at least a first direction along the first surface and wherein the first carrier comprises a material having a rigidity that maintains the first pattern of vias within a given threshold distortion following a given process conducted after the film is attached to the first support structure.

In some embodiments, the patch further comprises a module coupled to at least one of: the one or more microelectronic structures; and one or more of the vias. In some embodiments, the module provides power to at least a given one of the microelectronic structures. In some embodiments, the module provides power to the given microelectronic structures through at least a given one of the vias. In some embodiments, the module is configured to record a signal obtained using one or more of the microelectronic structures. In some embodiments, the patch further comprises a gasket formed on the first surface of the film, the gasket facilitating coupling of the module to the one or more microelectronic structures and the one or more vias.

In some embodiments, the patch further comprises at least one conductive trace connecting a first microelectronic structure formed on the second surface of the film with conductive material in a first one of the vias. In some embodiments, the first microelectronic structure comprises a body electrode.

In one embodiment, a method comprises providing a patch, the patch comprising a first support structure comprising an adhesive layer formed over a first carrier, a film attached to the first support structure and comprising a first pattern of two or more vias formed at least partially therethrough, a first surface of the film being bonded to the adhesive layer of the first support structure, one or more microelectronic structures, the one or more microelectronic structures being at least one of: formed in at least one of the vias; and formed as a pattern on a second surface of the film, the second surface of the film being opposite the first surface of the film, a surface adhesive formed over at least a portion of the second surface of the film, and a liner attached to the surface adhesive, wherein the film is stretchable in at least a first direction along the first surface and wherein the first carrier comprises a material having a rigidity that maintains the first pattern of vias within a given threshold distortion following a given process conducted after the film is attached to the first support structure. The method further comprises removing at least a portion of the liner to expose at least a first region of the surface adhesive, attaching the patch to a first structure by bonding the exposed first region of the surface adhesive to a first surface of the first structure, and removing at least a portion of the first carrier.

In some embodiments, the method further comprises removing a remaining portion of the liner after attaching the patch to the first structure to expose at least a second region of the surface adhesive and bonding the exposed second region of the surface adhesive to the first surface of the first structure.

In some embodiments, the method further comprises removing a remaining portion of the liner after attaching the patch to the first structure to expose at least a second region of the surface adhesive and bonding the exposed second region of the surface adhesive to a second surface of the first structure.

In some embodiments, the method further comprises removing a remaining portion of the liner after attaching the patch to the first structure to expose at least a second region of the surface adhesive and bonding the exposed second region of the surface adhesive to a first surface of a second structure.

In some embodiments, the first structure comprises skin of a subject, a container, or a product.

In some embodiments, the method further comprises providing a module and attaching the module to the patch to couple the module with at least one of: one or more of the microelectronic structures; and one or more of the vias. In some embodiments, the method further comprises providing power to one or more of the microelectronic structures from the module. In some embodiments, providing power to one or more of the microelectronic structures from the module comprises providing power to the microelectronic structures through at least one of the vias. In some embodiments, the method further comprises utilizing the module to record at least one signal obtained from the first structure using the one or more microelectronic structures.

BRIEF DESCRIPTION OF THE DRAWINGS

Several aspects of the disclosure can be better understood with reference to the following drawings. In the drawings, like reference numerals designate corresponding parts throughout the several views.

DETAILED DESCRIPTION

Figure 1:
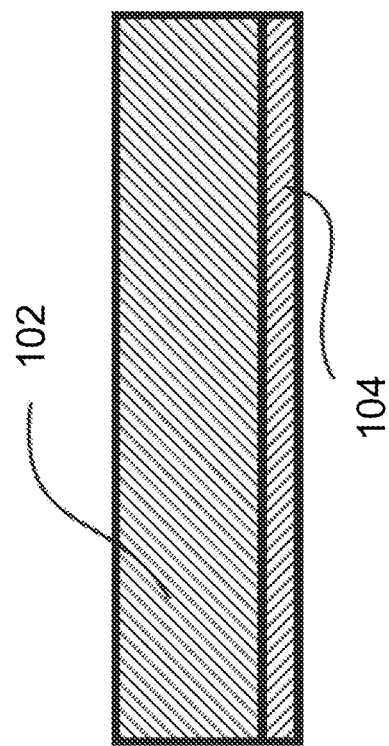
FIG. 1 shows a side cross-sectional view of a support structure including a film and a carrier, according to an embodiment of the invention.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

As described above, physiological monitoring is one application area wherein it is desired to provide small, lightweight and/or comfortable devices. As chronic diseases continue to proliferate throughout the world, there is a heightened need for early diagnosis, monitoring and treatment of such conditions in a cost effective and long-term acceptable manner. Remote monitoring of patients with cardiovascular diseases (heart failure, post stroke, etc.), sleep apnea, sleep disorders, diabetes, kidney failure, chronic obstructive pulmonary disease (COPD), obesity, neurological disorders (movement disorders, depression, Alzheimer's disease, migraines, stress disorders, etc.), and arthritis, among other ailments, for purposes of treatment or prevention of such diseases may substantially improve patient outcomes.

Although physiologic monitoring is performed today for a range of purposes, existing technologies are not without shortcomings.

There is a need to measure physiologic parameters of subjects reliably, simply, and without cables. As the proliferation of mobile and remote medicine increases, simplified and unobtrusive means for monitoring the physiologic parameters of a patient become more important.

Patient compliance is critical to the success of such systems and is often directly correlated to the ease of use and unobtrusiveness of the monitoring solution used.

Existing monitoring systems are often prone to false alarms, usage related failures, unreliable user interfaces, cumbersome interfaces, artifact or electromagnetic interconnect (EMI) related interference, etc. Such problems decrease productivity of using these systems, can result in lost data, and lead to dissatisfaction on the part of both the subject being monitored and the practitioners monitoring the subject. In the case of a hospital setting, the continual drone of alarms can lead to alarm fatigue and decreased productivity.

Long term compliance and data loss may suffer due to uncomfortable interfaces with monitoring devices, involved maintenance or change-over of disposables, painful or itchy reactions to materials in the devices, loss of functionality, and the like all of which may contribute to non-compliance and a break in usage of a particular device.

More reliable, redundant, and user friendly systems are needed that can provide valuable patient data even when operating with limited supervision, expert input, or user manipulation, and for prolonged nearly chronic usage periods.

Various embodiments described herein provide devices and techniques for forming devices which may be utilized in physiological monitoring to meet the above-described needs by providing thin film support structures. Such thin film support structures may provide bioadhesive devices or patches that include a film that is not stable or self-supporting in a freestanding state, yet is robust enough to provide a breathable and/or comfortable basis for supporting and interconnecting circuitry and sensing elements used in the monitoring of a subject. For example, the film may be soft, stretchable, breathable and elastically recoverable. By elastically recoverable, it is meant that the film may be reversibly deformed by stretching, contorting, etc. and returned to its original shape with only minor variation (e.g., within a defined tolerance such as less than 20%, less than 10%, less than 5% or the like). Reversible deformation may be preferred in certain use cases, such as in a patch for medical monitoring which may be placed over a joint or other portion of a subject that is repeatedly flexed during use. In other embodiments, the film may not be reversibly deformed, such as films that are made for single-use applications including single-use biometric applications. Regardless of whether an ultimate end product including a thin film structure is or is not reversibly deformed, it is desirable to provide a support structure for such thin films to facilitate fabrication and handling.

Thin film support structures may include a carrier or liner that is substantially stronger and less flexible than the film. Thin film support structures may have equivalent mechanical properties (e.g., an equivalent elastic modulus and/or equivalent flexural modulus) substantially equivalent to that of the carrier or liner, such that the thin film support structure is capable of supporting itself in the freestanding state. For example, in some embodiments a thin film support structure is capable of supporting its weight when held perpendicular to a gravitational field such that the thin film structure does not buckle back on itself. In other embodiments, the thin film support structure may be flexible or stretchable such that it is itself not self-supporting in a free-standing state. In such cases, the thin film support structure may be stretched, flexed, twisted, etc. but generally provides greater support or rigidity relative to the film by itself. The thin film support structure thus facilitates the ease of handling of the film and can also provide stability for subsequent manufacturing of structures including the film or other processing of the film, including but not limited to providing precision alignment for layer to layer registration, supporting of the layers during processing steps, increasing web strength and handle-ability of structures during fabrication, etc.

Thin film support structures may include a thin film stretchable interconnect, with the film having a pattern of one or more holes extending from a first surface to a second surface thereof. The holes may be formed while the film is attached to a first carrier that mechanically constrains the film during formation of the through holes therein. The film may then be transferred to a second carrier, exposing the second surface of the film. A set of patterned features may be formed on the second surface, with one or more of the patterned features electrically, optically or thermally coupling different through holes formed in the film. Microelectronic structures or other types of functional features may be formed in the through holes, or on one or more surfaces of the film. The functional features may, as an example, by electrodes configured to monitor physiological features of a subject.

It is important to note that while various embodiments will be described below in the context of devices and techniques for forming devices utilized in physiological monitoring, embodiments are not so limited. The techniques described herein may be used in various other application areas, including but not limited to forming microelectronic devices such as RFID tags, NFC tags, sensors, foldable antennas, wearable art, etc.

Various embodiments described herein permit the formation and maintenance of a pattern of structures and/or vias in a film during manufacturing and/or handling thereof. For example, films may be thermoplastic elastomers or elastomers that are extremely thin. Using the embodiments described herein, microelectronic circuits and other structures may be formed in such thin film elastomers, at scale, in a cost effective and reliable manner. Precision patterned microelectronic structures formed on or through films often requires exposure of the film to strong solvents and to temperatures whereby the films will, at the very least, soften and distort, but also potentially melt, anneal or partially dissolve. The techniques described herein permit formation of structures in such films even in light of these potential issues with exceptional precision and without damaging the delicate films.

Various processing may be carried out on panels or rolls. Panels may have tens to hundreds of parts on them, with each part requiring high precision placement of electronic microstructures. The alignment between layers forming such structures is often critical. Rolls may have thousands up to millions of parts, again with each part generally having strict precision placement requirements. Since thin films are not mechanically strong, without support the thin films would distort during handling during panel and/or roll processing, making the alignment and placement of microelectronic structures impossible or very difficult, and/or adversely affecting product yield.

Further, a thin film may be distorted if it is not supported when microelectronic structures are formed on the surface thereof or in vias or through holes formed through the film. This can lead to a number of issues, including but not limited to increasing the difficulty of layer-to-layer alignment, breakdown of the film due to solvent exposure, deformation near melting temperature, delamination from a carrier, etc. These and other issues can result in a multi-layer structure wherein the pattern of structures of layers do not align with one another. Further, it can be exceedingly hard to form electrical structures that connect to either surface of a thin film (e.g., through a via) as may be difficult to create through holes in thin films in a precise pattern. Yet another difficulty relates to forming microelectronic structures such that they do not lock up to a carrier during processing and storage, but adhere in a stable and controlled manner, such that they are not damaged or separated from the film when a carrier or liner is removed therefrom.

Embodiments provide techniques facilitating fabrication of thin film structures, overcoming one or more of the above-noted difficulties while maintaining excellent registration and with minimal distortion. Thus, thin film structures can be manufactured using processes such as roll-to-roll fabrication, which requires web tension at drying and/or curing temperatures. Also, thin film structures may be formed even when processing steps for manufacturing approach the softening point or melting point of the film itself, as some embodiments described herein allow for nearly undistorted feature registration, minimal thermal distortion of films, and removal of a film from a carrier after processing. Easy/reliable removal of the film from a carrier can be critical to increased product yield. For example, without easy removal there is a risk of distortion, damage to one or more microelectronic structures, residual stress, loss of registration to additional interconnects, curling, unreliable user application, adhesion of the film to the carrier, etc.

In some embodiments, a thin film support structure includes a first support structure having an adhesive layer formed over a first carrier, and a film attached to the first support structure by bonding a first surface of the film to the adhesive layer of the first support structure. The film is stretchable in at least a first direction along the first surface (e.g., in-plane). The film has a first pattern of one or more vias formed at least partially therethrough, and the first carrier is formed from a material that has sufficient rigidity such that the first pattern of vias is maintained within a given threshold distortion after processing or manufacturing involving the thin film support structure.

In some cases, the first pattern of vias may be formed while the film is attached to a second carrier. Generally, the second carrier should be mechanically stable such that via structures may be formed in the film without substantial distortion. Thus, the distance between features or the representative dimensions of features such as the vias does not change by more than the threshold amount if measured before and after processing. Formation of vias in the film while attached to the second carrier may, in some embodiments, be performed at or near room temperature and thus the second carrier need not necessarily have high thermal stability.

In some embodiments, the first carrier is generally more stable than the second carrier, at least in regards to thermal stability. The first carrier should meet distortion requirements while being subjected to web-tension or mechanical handling (e.g., from sheet feeding equipment, etc.) as well as during application of solvent laden inks, during exposure to thermal processes, etc. during production of a final structure. Tighter tolerance, or lower distortion, advantageously permits the use of greater web sizes, which can decreases costs associated with manufacturing thin film structures by permitting formation of microelectronic or other functional features in thin elastomeric films in high throughput processes.

Another challenge involves maintaining low tack adhesion between the first carrier or first support structure and the film during such processing so that the film can be released after completion without damage. For example, if standard casting paper were used as the second carrier, adhesion to the film may build up to an unacceptable level such that one cannot reliably release the film after completion without damaging the film or any functional features formed therein, or without overpowering a usage-based adhesive (e.g., without it being stronger than an actual adhesive used to bond a final product to a target structure).

While various embodiments are described herein wherein functional features such as microelectronic structures, conductive material, etc. are formed in vias of a film, embodiments are not limited to such arrangements. In some cases, functional features may be formed on a surface of the film, with the film being folded over to expose tabs and effectively create an attachment site. The attachment site may be used to connect a battery attachment, facilitating formation of light emitting and stretchable temporary tattoos, as one non-limiting example of a novel structure formed using the thin film support structures described herein. A folded over edge can be used to create the battery attachment. Alternatively, the battery or other power source may be provided via a hub or module that accesses, connects or is coupled to microcircuits or other functional features through vias formed in a film as described in further detail below. Creases and/or folds in a film may be formed so as to create a flexure in a resulting structure. A film may be folded along such creases and/or folds to create a multilayered structure from a single film, such as a foldable antenna in another non-limiting example of a novel structure formed using the thin film support structures described herein.

In some embodiments, vias are formed through a thin film to facilitate formation of thin film structures. In general, direct formation of kiss cut vias in a laminate may damage a carrier. Such damage may contribute to the formation of unreliable adhesion sites around via edges, may cause film liftup on edges, and can have issues relating to slug removal. Thus, some embodiments form holes in a film as through cuts and then transfer the film to a carrier thus transforming the through cuts into neat kiss cuts. This advantageously allows for formation of functional features on the film and in the vias formed in the film. It is difficult to precisely form functional features, as the functional features in some cases must be registered to the vias or formed or placed in the vias and over the via thresholds. If the vias are not well formed in the film and the film edges around the vias are not well adhered, the film can delaminate during processing or formation of the functional features. Also, if the pattern of vias is not well positioned, targets can be missed during layering of microelectronic structures and other functional features. The use of carriers in thin film support structures also provides mechanical support during film processing, in some cases keeping a film from sagging, distorting, etc. during processing.

Embodiments may also be used to facilitate formation of thin film structures permitting electrical communication through a film. Precisely patterned vias may be filled with conductive material, allowing connectors coupled to the bottom side of the film to interface with traces on a top side, or vice versa.

In some embodiments, functional features in the form of elastic multilayered circuits may be formed. The formation of multilayered elastic circuits is made possible using the techniques described herein by providing via structures or patterns of vias that can stretch with a device when placed on a structure or subject. Multilayered circuits can be created on an elastomeric substrate or film, such that the resulting thin film structure is stretchable. The thin film support structures may be used to maintain the integrity of circuits and layer-to-layer alignment during processing or manufacturing.

In some cases, a thin film structure is rendered nonfunctional if a crack forms in any of its vias. The thin film support structures described herein maintain functional integrity of conductive vias and traces during processing or manufacturing, as well as during handling, attachment or application to a structure or subject. During processing or manufacturing, it can be difficult to keep a film adhered to a carrier while preventing lock-up of via elements to the carrier, or of the film to the carrier since various processing may involve heating the film above its softening point which may lead to delamination or lockup to a carrier. Some embodiments provide a balance which preserves the integrity of electronic circuits or other functional features formed in a thin film structure by providing an adhesive strength between the film, vias and carrier to hold together during fabrication but not to cause tear out of vias when removing a carrier during application.

FIGS. 1-13 depict a process for forming a thin film support structure.

FIG. 1 shows a side cross-sectional view 100 of a structure including a carrier 102 bonded to a film 104. In some embodiments, the carrier 102 is biaxially oriented polypropylene (BOPP), although other materials may be used including but not limited to casting paper, a print receptive substrate, a siliconized liner, a polyester liner, a web-supporting material, or the like including variants, derivatives, combinations and laminates of these and other like materials. The film 104 may be polyurethane (PU), although other materials may be used including but not limited to an elastomer, a silicone rubber, a silicone gel, a fluorosilicone rubber, a fluoroelastomer, a perfluoroelastomer, a polyether block amide, an ethylene-vinyl acetate, a polybutadiene, butyl rubber (BR), a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, resilin, or the like including variants, derivatives, combinations and laminates of these and other like materials. The film 104 represents any film-formable material. In some embodiments, the film 104 is a thin, stretchable and breathable material. More generally, film 104 represents a thin, stretchable, breathable and/or elastically recoverable material. The film 104 may be made breathable by perforation, or by choosing a material that has a high moisture vapor transfer rate (MVTR). Materials with high MVTR are generally difficult to handle or process. Thin film support structures as described herein thus facilitate the use of such materials for a wide variety of applications.

The carrier 102 provides support for the film 104, allowing the film 104 to be prepared for further processing steps discussed in detail below. As described above, the film 104 may not be stable or self-supporting in a freestanding state. The carrier 102 may be stiffer or more rigid than the film 104, thus mechanically constraining the film 104 during formation of the through holes 106 and any other patterning that may be performed.

In some embodiments, the carrier 102 is approximately 0.125 millimeters (mm) thick. In other embodiments, the carrier 102 may vary in thickness from 0.025 to 1.0 mm thick, from 0.05 to 0.5 mm thick, from 0.075 to 0.2 mm thick, or the like. The film 104 may be approximately 0.002 to 0.5 mm thick in some embodiments. The thickness of film 104, however, may range in other embodiments from 0.0001 to 1 mm, from 0.005 to 0.05 mm, from 0.005 to 0.015 mm, or the like. More generally, the relative thickness of carrier 102 and film 104 may vary depending on the needs of a particular use case. It is important to note that FIG. 1 and other ones of the figures described below are not necessarily drawn to scale for ease of illustration.

Figure 2:
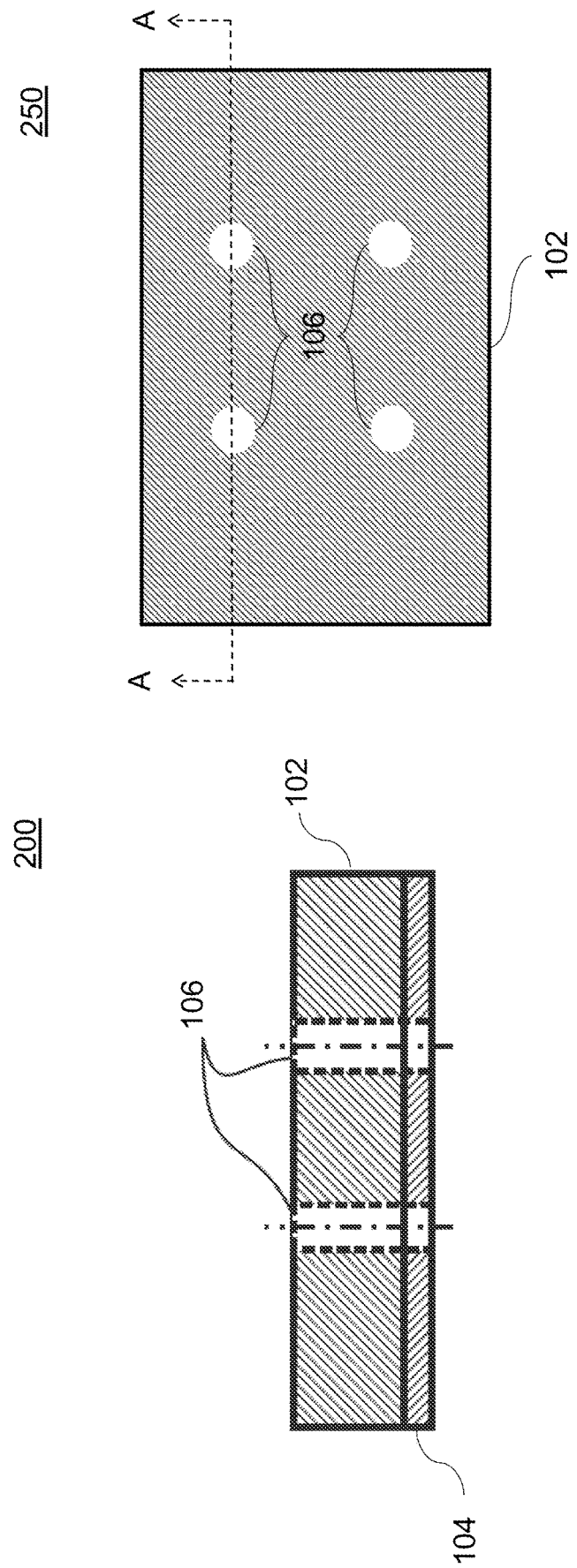
FIG. 2 shows a side cross-sectional view and a top view of the FIG. 1 structure following formation of through holes therein, according to an embodiment of the invention.

FIG. 2 shows a side cross-sectional view 200 and top view 250 of the FIG. 1 structure following formation of through holes 106 therein. The cross-sectional view 200 is taken along the line A-A shown in top view 250. The through holes 106 may be precision patterned, using various techniques including but not limited to die cutting, laser cutting, machining, milling, etching, chemical removal, thermal ablation, or the like. Although FIG. 2 shows the through holes 106 as being circular, embodiments are not so limited. In other embodiments, one or more of the through holes 106 may be circular, elliptical slits, star formations, rings, hole arrays, slit-star formations, square, rectangular, etc. In addition, while FIG. 2 shows each of the through holes 106 as being the same shape, embodiments are not so limited. In some embodiments, through holes of different shapes may be formed in the same structure. Also, while FIG. 2 shows an embodiment wherein there are four through holes 106 of equal size, embodiments are not so limited. A structure may have through holes of different sizes and different shapes formed therein.

In some embodiments, the through holes 106 are approximately 0.05 to 1.0 mm in diameter. In other embodiments, the through holes 106 may have a diameter or characteristic dimension ranging from 0.005 to 5 mm, from 0.01 to 1 mm, from 0.1 to 1 mm, or the like. In the FIG. 2 embodiments, the through holes 106 are formed completely through the film 104, but this is not a requirement. One of more of the through holes 104 may be formed as a via or trench that does not extend entirely through the film 104 and/or carrier 102. Also, in some embodiments a film may not have any through holes, vias or trenches formed therein.

Figure 3:
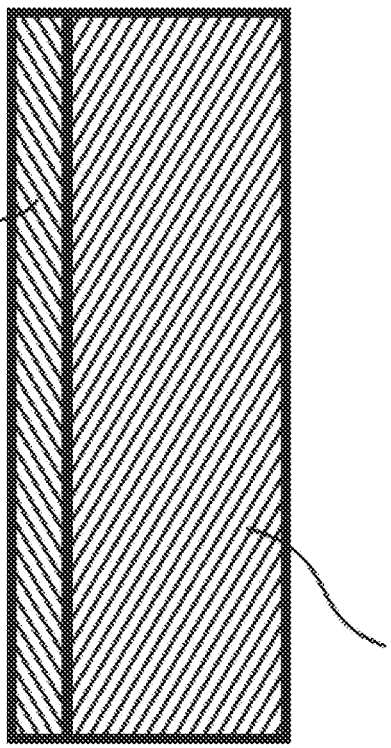
FIG. 3 shows a side cross-sectional view of another support structure including an adhesive and a carrier, according to an embodiment of the invention.
Figure 4:
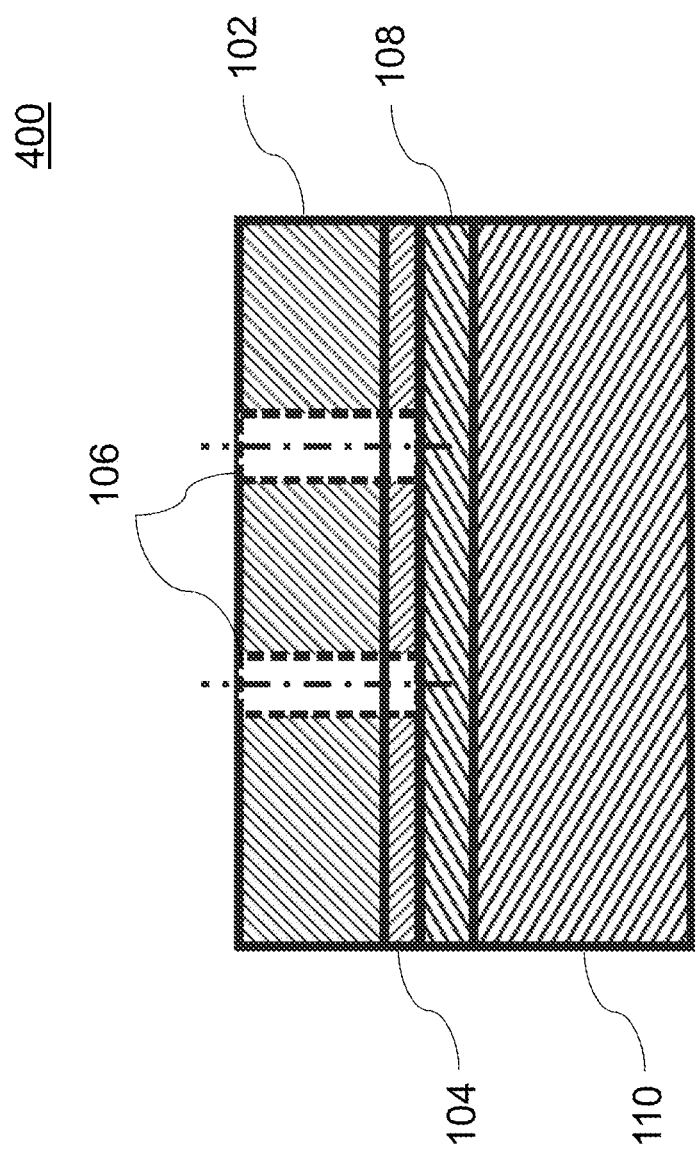
FIG. 4 shows a side cross-sectional view of a structure formed by laminating the FIG. 2 and FIG. 3 support structures together, according to an embodiment of the invention.

The film 104, in some embodiments, may be exchanged from carrier 102 to another carrier via a lamination process, also referred to herein as carrier exchange. The carrier exchange may be performed via sheet-to-sheet lamination, roll-to-roll lamination, etc. During carrier exchange, the film 104 may be tensioned as a result of tension applied to the web of a rolled process. FIGS. 3 and 4 described below illustrate an example of a carrier exchange process.

FIG. 3 shows a side cross-sectional view 300 of another structure including adhesive layer 108 and a carrier 110. The adhesive layer 108 may be low tack gel adhesive, and may be formed of various materials including but not limited to a crosslinked gel polymer, a pressure sensitive adhesive, a low tack adhesive, or the like. In some cases, the adhesive layer 108 may be a conducting layer such as a conducting particle filled adhesive, a z-axis conducting adhesive, or the like. The adhesive layer 108 may be sufficiently stable throughout all expected processing temperatures of the steps for processing the film 104 and forming functional features thereon. As will be discussed in further detail below, the FIG. 3 structure may be used with film 104 to form a folded structure such as a folded antenna. In such a case, the adhesive layer 108 may be a dielectric material.

In some embodiments, the adhesive layer 108 includes a friction lowering substance, possibly at trace levels, such that upon detachment of the adhesive layer 108 and carrier 110 from the film 104 the surface of the film 104 exhibits a low friction property. Examples of friction lowering substances that can be added to the adhesive layer 108 to achieve the low friction property include but are not limited to a polymer resin, an oil, an excipient, a blooming agent, a silicone oil, a wax, or the like. The low friction property is achieved, in some embodiments, as a thin residue remains on the film 104 after detachment of the carrier 110 and adhesive layer 108 from the film 104. This thin residue may render the film 104 very slick, and help to prevent rucking or edge lifting in a usage application. As will be described in further detail below, the film 104 may form part of a patch used for physiological monitoring. The thin residue that remains on the film 104 can reduce rucking on edges of such a patch that are exposed to a user. The thin residue or coating may have a thickness of essentially less than 1 µm, less than 0.25 µm, less than 0.2 µm, or the like and may be formed of a friction lowering substance as described herein. The thin residue or coating may also be useful in other application areas, such as in providing microelectronic structures that are attached to papers, containers, products, etc. for tracking, identification and other purposes.

The carrier 110 may be formed of biaxially-oriented polyethylene terephthalate (BoPET), although other materials may be used including but not limited to polyethylene naphthalate (PEN), biaxially-oriented PEN (BoPEN), polyethylene terephthalate (PET), polycarbonate (PC)/acrylonitrile butadiene styrene (ABS), PC/acrylonitrile styrene (AS), polybutylene naphthalate (PBN), polyimide (PI), polyphenylene sulfide (PPS), etc., including combinations, derivatives, variants and laminates of one or more of the above materials.

In some embodiments, the adhesive layer 108 is approximately 0.005 to 0.8 mm thick. In other embodiments, the adhesive layer 108 ranges in thickness from 0.001 to 1 mm, from 0.005 to 0.05 mm, from 0.005 to 0.015 mm, or the like. The carrier 110 in some embodiments is approximately 0.075 mm thick. In other embodiments, the carrier 110 ranges in thickness from 0.025 to 1.0 mm, from 0.05 to 0.5 mm, from 0.075 to 0.2 mm thick, or the like. In other embodiments, however, the relative thicknesses of the adhesive layer 108 and carrier 110 may vary depending on the needs of a particular use case.

The FIG. 3 structure is formed to provide a thermally stable, low tack carrier or support structure for film 104 as will be described in further detail below. As such, in some embodiments the FIG. 3 structure is cured at a high temperature, such as greater than 140° C., greater than 160° C., greater than 190° C., greater than 220° C., or the like, to shape-set, preshrink and/or stabilize the FIG. 3 structure for further processing steps to be described below. It is to be appreciated, however, that the FIG. 3 structure may be cured at other temperatures, such as temperatures in the range −20° C. to 400° C. More generally, in some embodiments it is desired to cure the FIG. 3 structure at as high a temperature as the materials used for the adhesive layer 108 and carrier 110 allow, or at a temperature exceeding the processing temperatures required to process the film 104.

In some embodiments, the film 104 may not be thermally stable in addition to not being mechanically stable or self-supporting in a freestanding state. By thermally stable, it is meant that a material substantially retains a basic shape during processing over a range of processing temperatures, e.g., from −20° C. to 250° C., from −20° C. to 160° C., from −20° C. to 120° C., etc. As will be described in further detail below, the carrier 110, which is thermally stable by virtue of the above-described curing process, provides a number of advantages in manufacturing devices including film 104. For example, since the film 104 is attached to a thermally stable carrier 110, the film 104 is mechanically constrained by the thermally stable carrier 110. As such, precision patterning and other processing may be performed on the film 104 so that even if the film 104 stretches or contorts during heating or other processing, the precision patterning would still line up for future processing steps including lamination, stacking, folding, etc.

For example, after attachment of the film 104 to the support structure including adhesive layer 108 and carrier 110, the resulting thin film support structure may be subject to various processing. The carrier 110 is able to maintain the pattern of vias within a defined threshold after such processing. For example, the carrier 110 may maintain the pattern of vias with distortion less than 1%, less than 0.25%, less than 0.1%, less than 0.01% or the like. The distortion may, in some embodiments, be less than 10 µm, less than 5 µm, less than 1 µm, or the like, either absolute or as measured relative to distances between centers or other critical or characteristic dimensions of adjacent ones of the vias formed in film 104.

The carrier 110, in some embodiments, is able to maintain the pattern within some defined threshold distortion due in part to mechanical properties and/or thermal stability of the carrier 110. For example, the elastic modulus such as the elastic secant modulus of the carrier 110 may be five times greater than the elastic modulus of the film 104, ten times greater than the elastic modulus of the film 104, fifty times greater than the elastic modulus of the film 104, one hundred times greater than the elastic modulus of the film 104, five hundred times greater than the elastic modulus of the film 104, or the like.

As a specific example, the film 104 may have a 100% elastic secant modulus less than 1000 MPa, less than 500 MPa, less than 100 MPa, less than 10 MPa, less than 1 MPa, or the like as defined using ASTM D790 Procedure B. In some embodiments, it is preferred for the film 104 to have an elastic modulus in the range of 5 to 75 MPa and preferably less than 50 MPa. It is important to note, however, that the film 104 and/or carrier 110 may have anisotropic properties, such that this elastic secant modulus may be different in different directions. Swelling or shrinkage may be in a principle direction or cross directions, and torsional distortion may also occur because of differential tension applied to the film 104, e.g., while the film 104 is pulled through roll-to-roll handling equipment. Also, while this specific example gives numbers in terms of a 100% secant modulus, materials may not have a 100% secant modules as fracture could occur prior to 100% strain. Alternatively, a tangent modulus, elastic model, stress at a given strain, or the like may be used to characterize the mechanical properties of the film 104 and/or carrier 110.

If the elastic modulus, as defined using a secant approach, is low, then it is mechanically difficult to handle the film 104, as any forces associated with handling the film 104 may stretch or distort the pattern of vias or through holes 106 that are registered to for patterning functional features as will be described in further detail below. Also, heating the film 104 may cause further softening, expansion or contraction, sagging, residual stresses, molecular reorganization, etc., which can further compound difficulties associated with creating a precisely registered series of images or artwork over one another on the film 104, and release thereof from the carrier during use, particularly in cost effective manufacture processes.

The carrier 110 provides rigidity in the thin film support structure, such that after attachment of the film 104 to the adhesive layer 108, the thin film support structure may be exposed to various processing without permanent distortion of the pattern of vias or through holes 106 formed in the film. For example, such processing may include heating the thin film support structure to a temperature greater than 100° C., greater than 120° C., greater than 140° C., greater than 160° C., greater than 180° C. or the like for at least one minute, at least two minutes, at least five minutes, at least ten minutes or the like. Such processing may additionally or alternatively include cooling the thin film support structure to a temperature less than 5° C., less than 0° C., less than −10° C., less than −15° C. or the like for at least five seconds, at least thirty seconds, at least one minute, at least two minutes or the like. The processing may also or alternatively include pulling the film 104 along a web, roll-to-roll processing of the film 104, etc.

In some embodiments, as will be described in further detail below, additional features may be formed over the adhesive layer 108 prior to further processing. As one example, a gasket may be formed over at least a portion of the adhesive layer 108. The gasket may be used to facilitate attachment of a thin film structure to other devices (e.g., module 30 described in further detail below with respect to FIG. 17). Various other types of features may be formed over at least a portion of the adhesive layer 108 in other embodiments depending on the use case, including but not limited to electric features, capacitive elements, resistive elements, touch sensitive components, flexible display elements, pixels, analyte sensing elements, printed electrochemical sensors, touch sensitive electrodes, light sensitive sensing elements, or the like. Further, in some embodiments, such features may be alternatively attached to or formed on the film 104 prior to the carrier exchange, such that the features are formed underneath the adhesive layer 108.

Although not specifically shown for clarity, the FIG. 3 structure may have patterned features such as split liners so as to facilitate the later ease of installation or attachment of film 104 to another structure or device. Examples of split features will be shown in FIGS. 11-15 and described in further detail below. In some cases, the formation of such split features is performed before the FIG. 3 structure is bonded or otherwise attached to the FIG. 2 structure for ease of manufacturing. For example, certain processes used for forming the splits, such as cutting, dicing, etc., may be more difficult to perform once the FIG. 3 structure is bonded or otherwise attached to the FIG. 2 structure. In cases where the FIG. 3 structure is cut or split prior to further processing, the FIG. 3 structure is still held together via material between the split features.

FIG. 4 shows a side cross-sectional view 400 of a structure formed by attaching the FIG. 2 structure to the FIG. 3 structure as illustrated. In some embodiments, the FIG. 2 structure and FIG. 3 structure are laminated together. The lamination process may utilize heat, pressure, welding, adhesives, etc.

Figure 5:
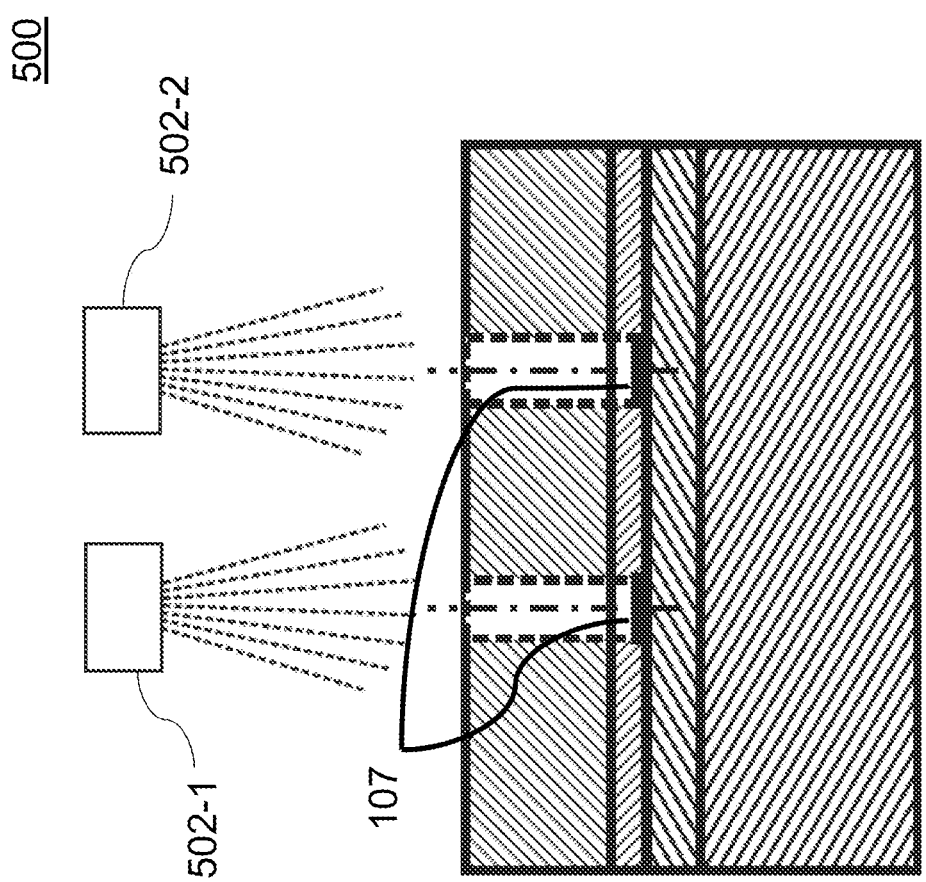
FIG. 5 shows a side cross-sectional view illustrating treatment of exposed regions in the FIG. 4 structure, according to an embodiment of the invention.

FIG. 5 shows a side cross-sectional view 500 illustrating application of a spray treatment to the exposed regions of adhesive layer 108 through the through holes 106 in film 104 prior to removing carrier 102. FIG. 5 shows material 107 deposited via spray dispensers 502-1 and 502-2. The material 107, in some embodiments, may be a release coating or a conductive medium. Some non-limiting examples of release coatings include siliconized release coatings, mold release mediums, wax, etc. The conductive medium may be an electrically and/or thermally conductive medium.

Although FIG. 5 shows the use of spray dispensers 502-1 and 502-2, collectively referred to herein spray dispensers 502, embodiments are not limited to this arrangement. For example, other techniques may be used to deposit material 107 in the exposed regions of the adhesive layer 108, including but not limited to painting, airbrushing, drop depositing, sputtering, physical vapor depositing, electrochemically plating, etc.

The carrier 102 provides a suitable mask for the treatment or coating of the exposed regions in the FIG. 4 structure, e.g., the regions exposed by through holes 106. Treating or coating the exposed regions in the FIG. 4 structure may provide a number of advantages, including but not limited to providing a releasable structure, a fiduciary mark, a via support material, a protective coating, a slip coating, a conductive release coating, an electrically conductive release coating, etc.

In some embodiments, the material 107 is approximately 0.1 μm thick, but may generally range from 0.01 to 100 μm thick, from 0.05 to 25 μm thick, from 0.05 to 1 μm thick, or the like. The thickness of material 107, however, may vary depending on the needs of a particular use case. For example, if the release is super thin, the material 107 may be less than 1 μm thick. If the material 107 is a conductive fill material, it may be the same thickness as film 104.

The material 107, which may be conductive material, adheres more strongly to the film 104 relative to the adhesive layer 108 or any release coating formed on the adhesive layer 108. By way of example the conductive material may have an adhesive strength to the adhesive layer 108 or a release coating formed on the adhesive layer 108 of less than 75 grams per inch (g/in), less than 50 g/in, less than 25 g/in, less than 10 g/in, or the like.

Figure 6:
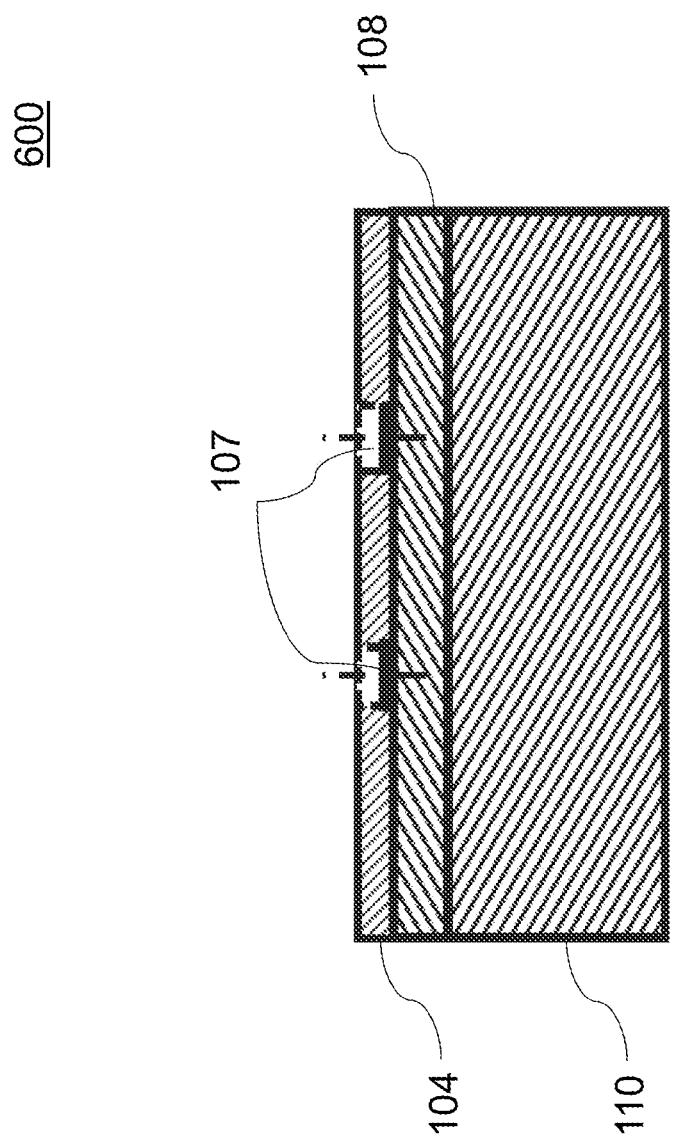
FIG. 6 shows a side cross-sectional view of the FIG. 5 structure following removal of the top carrier, according to an embodiment of the invention.

FIG. 6 shows a side cross-sectional view 600 formed by removal of the carrier 102 from the FIG. 5 structure. In some embodiments, peeling, chemical removal, thermal delamination, or the like may be used to remove the carrier 102 from the FIG. 5 structure. Various other processes may be used to remove the carrier 102, including but not limited to peeling, chemically assisted delamination, thermally assisted delamination, or the like.

Figure 7:
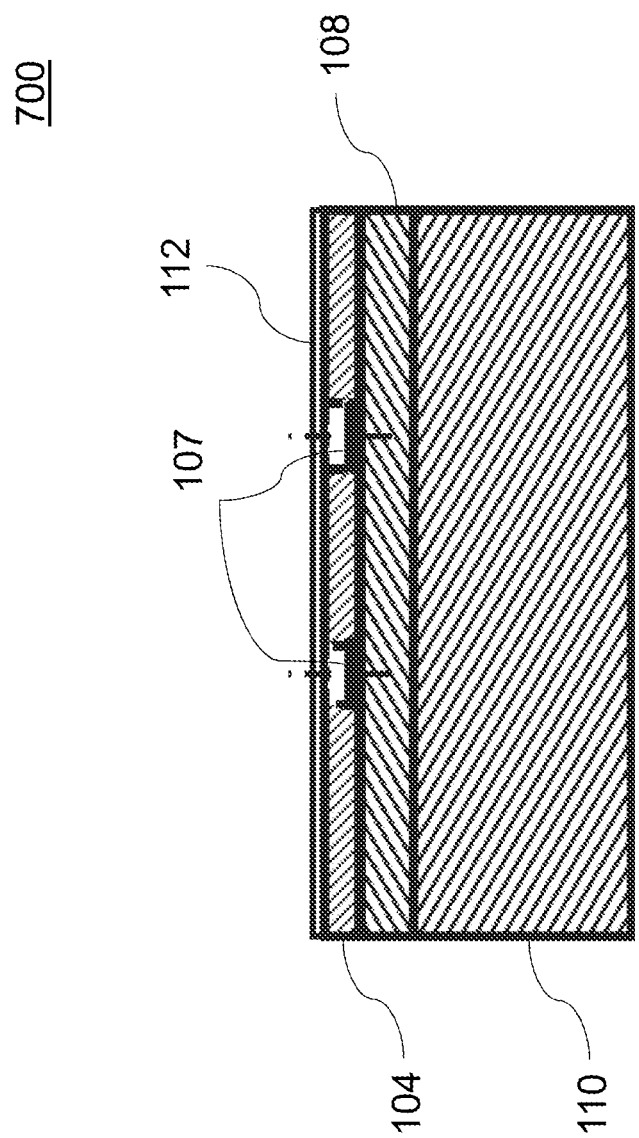
FIG. 7 shows a side cross-sectional view of priming a top surface of the FIG. 6 structure, according to an embodiment of the invention.

The top of the FIG. 6 structure may be subject to further processing in some embodiments. For example, FIG. 7 shows a side cross-sectional view 700 of a priming surface 112 formed over the FIG. 6 structure. The priming surface 112 may be formed using various techniques including but not limited to spraying, wiping, painting, emersion, etc. The priming surface 112 may be an organometallic self-assembled monolayer, although other materials may be used in other embodiments including but not limited to a titanate, a zirconate, an aluminate, an organosilane, a silane, a siloxane, or the like. The priming surface 112 provides a number of advantages for facilitating further processing of the structure 700, including but not limited to increased adhesion of features to the film 104, altered wetting of the surface of the film 104, color change indicators, etc.

In some embodiments, the priming surface 112 is approximately 0.01 to 0.1 μm thick. The thickness of the priming surface 112, however may vary depending on the needs of a particular use case. As an example, in some embodiments the priming surface 112 may be a thin priming layer that is applied differentially to promote adhesion to an organic region of the surface and not to an inorganic region of the film 104. As another example, the priming surface 112 may, in some embodiments, be a sputtered or physical vapor deposition (PVD) metallic layer, or a seeding layer for an electroless plating process the thickness of which may be in the range of 0.05 to 2 μm. In such cases, the priming surface 112 may serve as a basis for a conducting feature on the surface, as a shield or insulator, etc.

Further, in some embodiments the priming surface 112 may be applied to regions of the film 104 only, such as through a mask. The priming surface 112 may in other embodiments be formed everywhere on the surface of the film 104. Further features may be selectively patterned by an additional process so as to form treated regions on the surface of the film 104.

The FIG. 6 and FIG. 7 structures may also be referred to herein as support structures. Such support structures provide an integrated support for use in a variety of different applications. For example, these support structures may be used to form patches or thin stretchable interconnects for use in modular physiological monitoring systems, in heating pads, etc. The support structures may also be used to form various microelectronic products such as radio frequency identification (RFID) tags, near field communication (NFC) tags, sensors, foldable antenna structures, etc.

Advantageously, the support structures allow for formation of patches, thin stretchable interconnects and other micro-electronic products with a number of desirable properties such as ease of manufacturing. Such structures may be used to form tamper-proof stickers, or the like, wherein the films are sufficiently weak, such that they cannot be tampered with, without accidentally altering one or more properties thereof or irreversibly damaging them in some way or another during use. In some embodiments, such structures may be used to form cosmetic films, durable temporary tattoos with extended wear-time, and/or enhanced color fastness, etc. In some embodiments, the film 104 of such support structures may be used to form one or more aspects of a biometric identifying patch, to be worn by a subject, the removal of which is a recordable and/or substantially irreversible event.

The support structures shows in FIGS. 6 and 7 facilitate ease of manufacturing in a number of ways. For example, the support structures provide a thermally stable structure that can generally retain its shape. Thus, the film 104 may be prepared for such processing by the formation of the through holes 106 as described above, with the number, locations and shapes of such through holes 106 facilitating the formation of functional features for a desired end product. Such an approach allows for the formation of products with sufficiently thin, soft, and breathable films 104 so as to be worn long-term by a subject (days, weeks, etc.), which would otherwise be challenging to fabricate due to the delicate nature of the film 104.

The support structures shown in FIGS. 6 and 7 also facilitate ease of manufacturing in that these structures can be used with roll-to-roll processing techniques. As such, the support structures may be used for efficient production of hundreds of thousands or millions of end-products, with the support structures providing combined mechanical and thermal stability needed to survive the rigors of the roll-to-roll manufacturing process.

Film 104, by itself, is not typically suitable for many manufacturing processes. For example, the film 104 may be formed from a thermoplastic elastomer PU which is not typically thermally stable or able to retain its shape through processing operations such as described herein. Accordingly, embodiments which utilize support structures shown in FIGS. 6 and 7 allow for the use of thermoplastic elastomer PU as a suitable material for film 104.

In some embodiments, the support structures of FIGS. 6 and 7 are used to form patches that are placed onto an organic body, such as on the skin of a human body. Such organic bodies can bend, twist, stretch, contort, etc., and may also require oxygen and moisture exchange with the surrounding environment as well as other mass transfer functions. If the film 104 is merely flexible without being recoverably stretchable, it will pull, delaminate, etc. from the surface during such twisting, stretching, contorting, etc. Furthermore, the stresses experienced at the interface between the film 104 and the organic body during such actions may be "felt" by a user, thus reducing comfort, causing skin irritation or skin damage, etc. Also, if the film 104 has limited mass transfer capabilities such as limited moisture vapor transfer rate, the film can be prone to causing maceration or other skin conditions during use. For example, if moisture and/or gas exchange is not sufficiently high, wearing a thin film structure including film 104 may cause itching, reduced comfort, rashes, skin damage, maceration, making the site prone to infection, etc.

Figure 8:
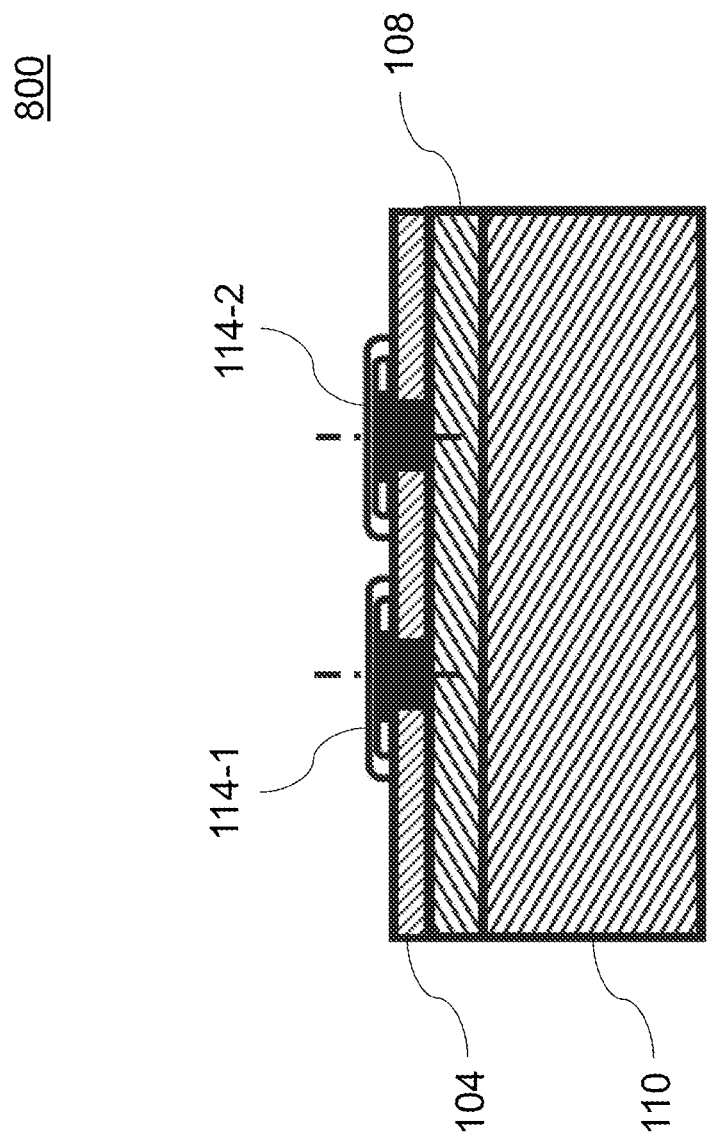
FIG. 8 shows a side cross-sectional view of functional features formed in through holes of the FIG. 6 structure, according to an embodiment of the invention.

FIG. 8 shows a side cross-sectional view 800 showing formation of functional features 114-1 and 114-2 on the FIG. 6 support structure. The functional features 114-1 and 114-2, collectively referred to herein as functional features 114, may be formed using a variety of different manufacturing processes including but not limited to printing, transfer lamination, dispensing, coating, blanket coating, vapor deposition, physical vapor deposition (PVD), spraying, sputtering, electroplating, submersion plating, electroless plating, self-assembly processes, etc. The functional features 114 may be formed registered to or aligned with the through holes 106 or vias in film 104, with the registration being within 1 mm, within 0.5 mm, within 0.25 mm, within 0.1 mm, within 0.05 mm, within 0.025 mm or the like of a preferred positioning.

The functional features 114 may be formed from one or more layers. As an example, each of the functional features may be formed from 1-8 layers of different materials, although other numbers of layers may be used in other embodiments. Individual layers of the functional features 114 may have a thickness of less than 50 micrometers (μm), less than 25 μm, less than 18 μm, less than 12 μm, less than 9 μm, less than 6 μm, less than 1 μm, or the like.

In embodiments, the functional features 114 may have an equivalent bulk elastic modulus of less than 900 megapascals (MPa), less than 500 MPa, less than 250 MPa, less than 100 MPa, less than 10 MPa, less than 1 MPa, or the like.

In embodiments, the functional features 114 may have an equivalent flexural modulus of less than 1 gigapascals (GPa), less than 0.5 GPa, less than 0.1 GPa, less than 0.01 GPa, or the like (i.e. as tested in accordance with an ASTM D790 or ISO 178 test protocol or substantially similar procedure).

In embodiments, the functional features 114 may have a moisture vapor transfer rate (MVTR) of greater than 50 grams per meters square per day ($g/m^2/day$), greater than 150 $g/m^2/day$, greater than 400 $g/m^2/day$, greater than 800 $g/m^2/day$, greater than 1000 $g/m^2/day$, greater than 4000 $g/m^2/day$, or the like. Elevated or larger MVTR may be advantageous for forming wearable microelectronic structures for placement over a region of skin of a subject for long-term wear or monitoring.

Different functional features 114 may use different numbers or arrangements of layers to form different types of functional features. By way of example, functional feature 114-1 may comprise an electrode of a first type while the functional feature 114-2 may comprise an electrode of a second type different than the first type.

The functional features 114, as shown in FIG. 8, extend from the top to the bottom surface of the film 104. Thus, the functional features 114 will not be exposed until later removal of carrier 110 and carrier 120 (to be described in further detail below). The functional features 114 fill the through holes 106 or vias that were previously formed through the film 104. The functional features 114, also referred to herein as filled vias, may be formed so as to be semi-conducting, electrically conducting, thermally conducting, ferromagnetic, ionically conducting, or the like. In some embodiments, the filled vias may be electrically conducting, such that the impedance through the filled via is less than 1000 ohm (Ω), less than 100Ω, less than 10Ω, less than 1Ω, less than 0.1Ω, less than 0.01Ω, or the like.

Figure 18:
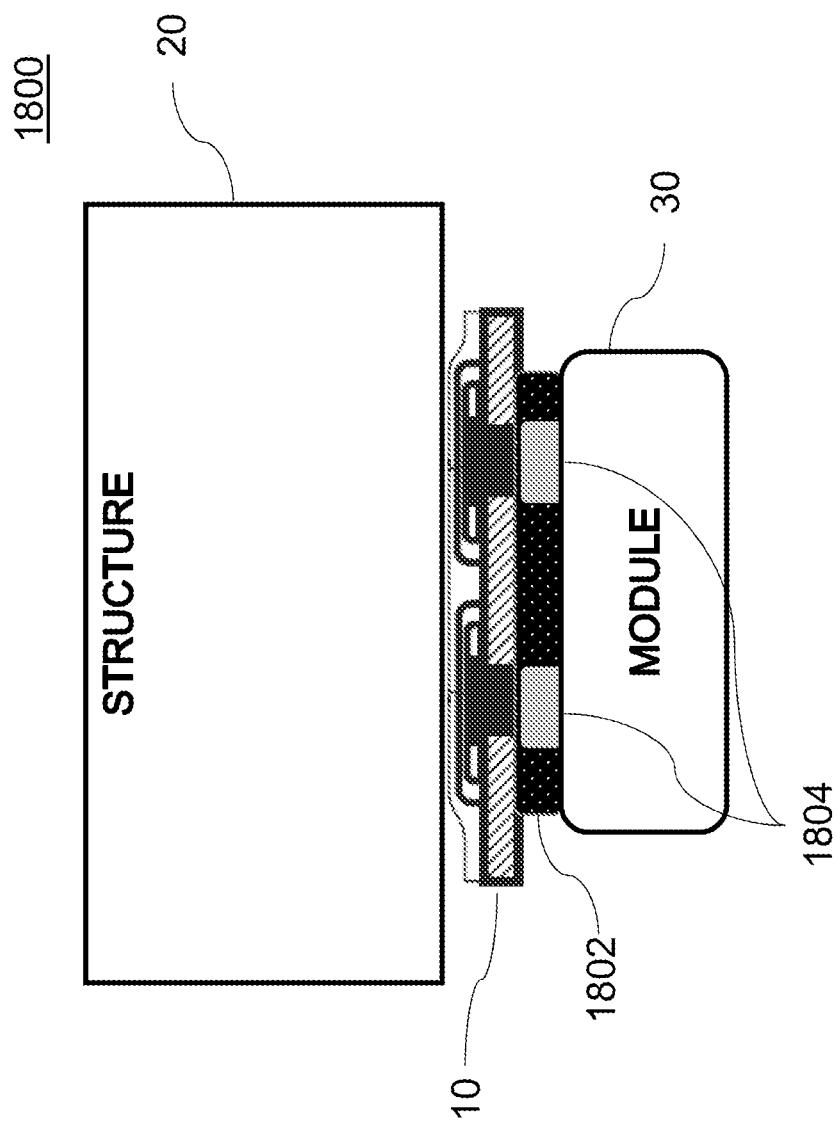
FIG. 18 shows a side cross-sectional view of the FIG. 16 structure attached to a module using a gasket, according to an embodiment of the invention.
Figure 19:
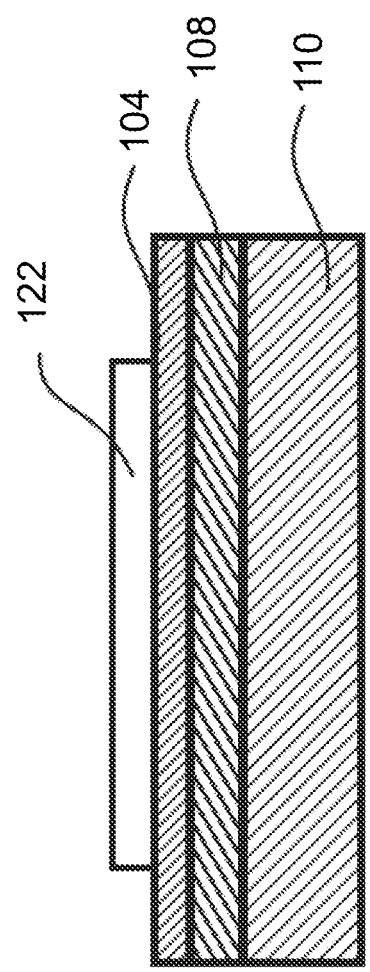
FIG. 19 shows a side cross-sectional view of portions of a thin film support structure before formation of a wrinkle pattern in a conducting layer formed thereon, according to an embodiment of the invention.

The functional features 114 are shown in the FIG. 8 structure as being formed at least partially in the through holes 106 of film 104 or coupled thereto. As shown, however, the functional features 114 may also be at least partially formed on a top side of film 104 around the through holes 106. In other embodiments, one or more functional features may also be formed on the top side of the film 104 away from the through holes 106. Although not explicitly shown in FIG. 8, the functional features 114-1 and 114-2 may be interconnected via additional functional layers formed on a top side of the film 104 connecting the through holes 106. In some embodiments, one or more of the functional layers may be conducting layers that have wrinkles formed therein to create patterned traces that are stretchable. FIGS. 18 and 19 illustrate forming of such patterned traces.

The thickness and width of the functional features 114 will vary depending on the use case and the type of functional feature formed. As an example, one or more of the functional features 114 may be needle electrodes that are designed to penetrate through the surface of a corresponding structure, and thus may be thicker or protrude further away from the top side of the film 104 relative to other types of functional features. Various other examples are possible including but not limited to electrical traces, stretch sensing elements, electrodes, ionically conducting electrodes, reference electrodes, contact interfaces, conduits, microfluidic channels, antennas, stretch resistant features, stretch vulnerable features (e.g., a feature that changes properties reversibly or irreversibly with stretch), strain sensing elements, photo-emitters, photodiodes, biasing features, bumps, graphic images, touch sensors, pressure sensing elements, interfacial pressure sensing elements, piezoelectric elements, piezoresistive elements, chemical sensing elements, electrochemical cells, electrochemical electrodes or sensors, electrical interconnects, thin-film insulation, medical compositions, drug delivery regions, light emitting pixels, flexible displays, light emitting temporary tattoos, light emitting diodes (LEDs), flexible LEDs, redox reactive sensing electrodes, light sensitive structures, moisture sensitive structures, pressure sensitive structures, magnetic structures, or the like.

The functional features 114 may provide numerous different or related functions. For example, the functional features 114 may be stretchable electrical traces, liquid metal features, non-stretchable electrical traces, sensory features, chemical sensing features, magnetic features, human interface features such as electrodes, microneedles, cannulas, etc., adhesives, bioadhesives, antennas, transistors, integrated circuits, transceivers, sacrificial structures, water soluble structures, temperature sensitive structures, light sensitive structures, light degrading structures, flexible light emitting elements, piezoresistive elements, moisture sensitive elements, mass transfer altering elements, etc. In one embodiment, one or more of the functional features 114 may have a controlled mass transfer property, such as a controlled moisture vapor conductivity so as to allow for a differential heat flux measurement through the film 104, when such a region is used in conjunction with a plurality of temperature sensors embedded into the film 104, one or more features thereupon, in an accompanying module, or the like.

Figure 9:
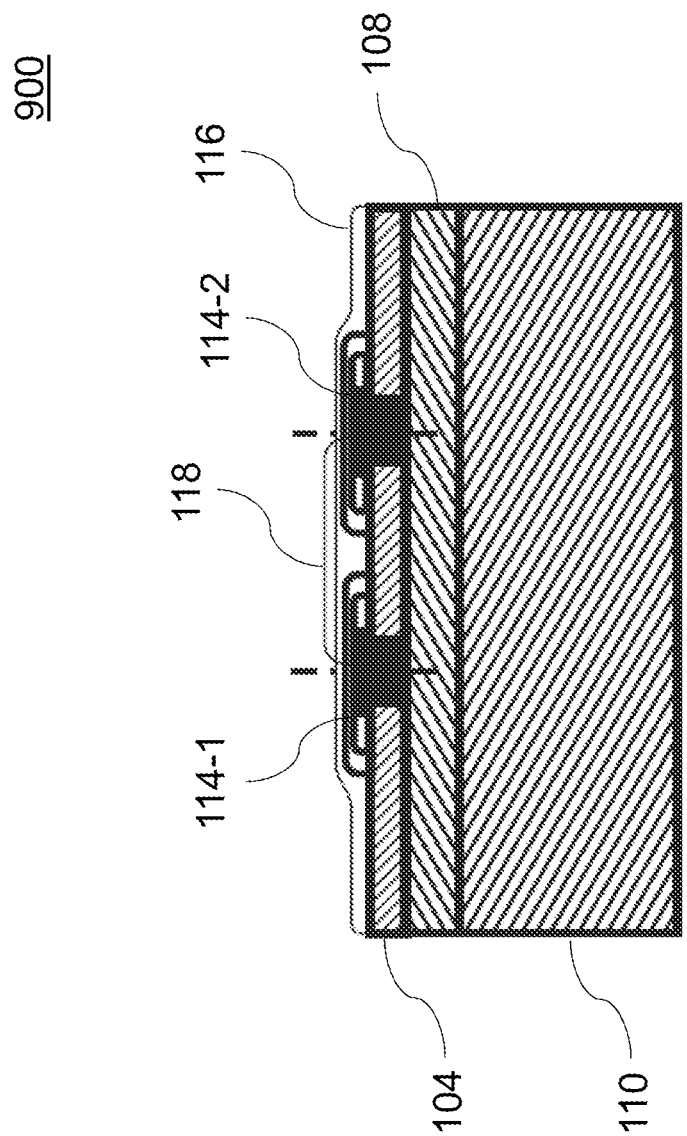
FIG. 9 shows a side cross-sectional view of additional functional features formed on the FIG. 8 structure, according to an embodiment of the invention.

FIG. 9 shows a side cross-sectional view 900 of the FIG. 8 structure following formation of additional functional layers 116 and 118. Similar to the functional features 114, the functional layers 116 and 118 may be formed using one of or a combination of various different manufacturing processes including but not limited to printing, transfer lamination, dispensing, coating, blanket coating, sputtering, physical vapor deposition, electroless plating, extrusion coating, gravure printing, lamination, etc. In some embodiments, one or both of the functional layers 116 and 118 may be patterned traces that couple different ones of the functional features 114 together.

The FIG. 9 structure, in some embodiments, may be folded against itself to form a multi-layered, folded structure. For example, the FIG. 9 structure may be folded repeatedly on itself after removal of carrier 110 to form a folded or multi-layer antenna of other micro-electronic device. Such folding may be performed to create one or more precisely defined microchannels within the structure to form, for example a micro-cannula, a microchannel for drug delivery, for fluid transfer, or the like. Such channels may be advantageous for communicating a fluid (i.e. a drug, a medical composition, insulin, an analyte, an interstitial fluid, sweat, glucose, etc.), between a site on a subject (i.e. a microneedle site, a microcannula site, an injection site, a sweat gland, etc.), to one or more sites on the film or a module coupled thereto (i.e. a reservoir, a drug reservoir, a sensor, a glucose sensor, a lactate sensor, etc.), or the like.

Figure 10:
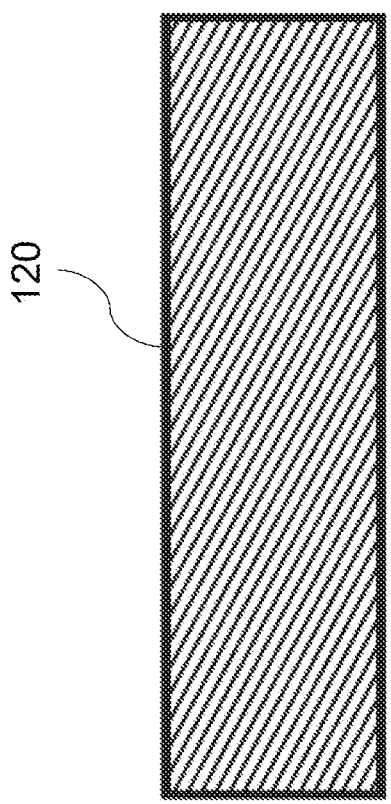
FIG. 10 shows a side cross-sectional view of another support structure, according to an embodiment of the invention.

FIG. 10 shows a side cross-sectional view 1000, which includes an additional carrier 120 which may be attached to the FIG. 9 structure. The carrier 120 may be formed of BoPET, although other materials may be used including but not limited to PEN, PET, BoPEN, PC/ABS, PC/AS, PBN, PPS, polycarbonate, polyethylene, release paper, siliconized release paper, a barrier film, polypropylene, BoPP, or the like. It is important to note, however, that embodiments need not necessarily include the additional carrier 120 in a resulting structure as will be described in further detail below.

In some embodiments, the carrier 120 is approximately 0.125 mm thick. The thickness of the carrier 120, however may vary depending on the needs of a particular use case, such as between 0.015 mm to 0.15 mm in some embodiments.

Although not specifically shown for clarity, the FIG. 10 structure may be split or split in patterns so as to facilitate the later ease of installation or attachment of a thin film structure including film 104 to another structure or device. In some cases, the formation of such splits is performed before the FIG. 10 structure is bonded or otherwise attached to the FIG. 9 structure for ease of manufacturing. For example, certain processes used for forming the splits, such as cutting, dicing, etc., may be more difficult to perform once the FIG. 10 structure is bonded or otherwise attached to the FIG. 9 structure. In cases where the FIG. 10 structure is cut or split prior to further processing, the FIG. 10 structure is still held together via continuous material between the split features. For example, the splits may be formed in patterns, such as multiple ribbons brought in together along a web, may be split but temporarily held together with tape, etc.

Figure 11:
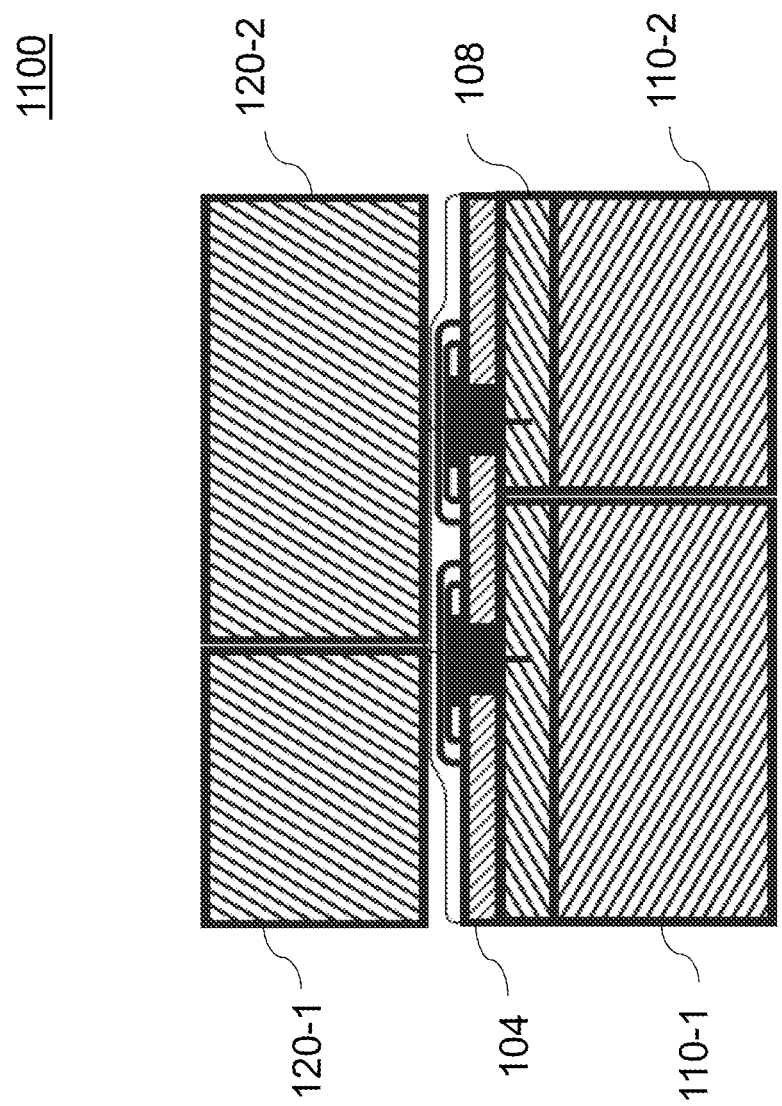
FIG. 11 shows a side cross-sectional view of a structure formed by laminating the FIG. 8 and the FIG. 9 structures together and forming splits in the top and bottom carriers, according to an embodiment of the invention.

FIG. 11 shows a side cross-sectional view 1100 formed by attaching the FIG. 9 structure to the FIG. 10 structure as illustrated. In some embodiments, the FIG. 9 structure and FIG. 10 structure are laminated together. The lamination process may utilize heat, pressure, welding, adhesives, etc. FIG. 11 also shows that carrier 110 is split into 110-1 and 110-2, and that carrier 120 is split into 120-1 and 120-2. The formation of such split carriers, also referred to herein as split liners, facilitates easy release of the carriers 110 and 120 when attaching the remainder of the FIG. 11 structure to other structures, modules, etc. as will be described in further detail below with respect to FIGS. 13-17.

Figure 12:
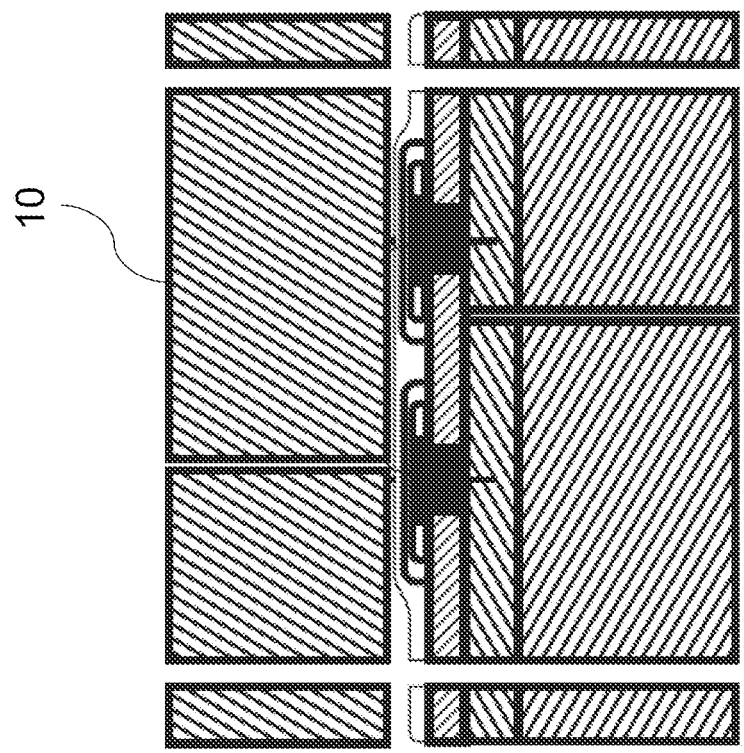
FIG. 12 shows a side cross-sectional view of singulation of a thin film support structure from the FIG. 11 structure, according to an embodiment of the invention.
Figure 13:
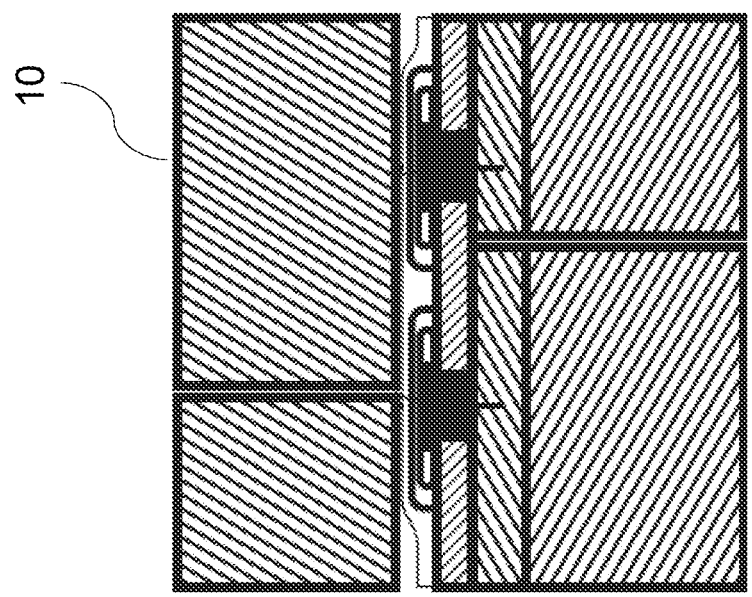
FIG. 13 shows a side cross-sectional view of a thin film support structure, according to an embodiment of the invention.

FIG. 12 shows a side cross-sectional view 1200 of singulation of the FIG. 11 structure into an end product, such as resulting structure 10. FIG. 13 shows a side cross-sectional view of structure the resulting structure 10 formed by singulation as illustrated in FIG. 12. While various embodiments are described below in the context of the resulting structure 10 being used as a patch for physiological monitoring, embodiments are not limited to this arrangement. By way of example, the resulting structure 10 may be used as an RFID tag, NFC tag or other sensor for attachment to products or other items to facilitate tracking goods in a supply chain, as well as devices for use in various other applications described herein. For example, the resulting structure 10 may be used as part of a biometric device or a single use, destructably removable identification device. Such a device may be coupled with a chipset to identify a user upon which it is placed. It may include one or more sensing elements to monitor the subject, monitor the quality of the contact with the subject, etc. so as to record any tampering. The device may be suitable for providing a temporary and single use user identification code, or the like.

The microelectronic structures or functional features 114 may include a bioadhesive for attachment to a surface, such as the skin of a subject. Other types of adhesives may be utilized for other use cases depending on the object or structure to which the functional features are to be attached. The film 104, with the functional features 114 formed therein, may be sufficiently fragile such that it is not stable in a freestanding state, e.g., the structure may flex, twist, stick together when flexed, etc. such that the functional features 114 are rendered non-functional or effectively non-functional. The use of carriers or liners, such as carrier 110 and carrier 120, supports the film 104 and functional features 114 of the resulting structure 10 during the manufacturing and handling thereof to provide precision alignment of layer to layer registration, support of the layers during processing steps, increasing web strength and handle-ability of the structures during fabrication, etc.

The support structures, such as carrier 110 and carrier 120, are substantially stronger and less flexible than the freestanding layers of the resulting structure 10 including the film 104 and functional features 114. The support structures, for example, may have an equivalent elastic modulus of greater than 500 MPa, greater than 1 GPa, greater than 1.5 GPa, greater than 3 GPa, or the like. The support structures may have an equivalent thickness of greater than 12 µm greater than 25 µm, greater than 35 µm, greater than 50 µm, greater than 100 µm, or the like. The support structures have may have an equivalent flexural modulus of greater than 1 GPa, greater than 2 GPa, greater than 3 GPa, greater than 5 GPa, or the like (i.e. as tested in accordance with an ASTM D790 or ISO 178 test protocol or substantially similar procedure).

The combination of the carriers 110 and 120 with the film 104 and other freestanding layers provides a thin film support structure in the resulting structure 10. In some embodiments, the equivalent mechanical properties of the resulting structure 10 are substantially equivalent to that of the support structures formed therein, such that the resulting structure 10 with the carriers 110 and 120 attached thereto is capable of supporting its own weight when held perpendicular to a gravitational field such that the resulting structure 10 does not buckle back on itself. In other embodiments, the resulting structure 10 may still be somewhat flexible such that it is not freestanding when held perpendicular to a gravitational field while maintaining sufficient rigidity such that the microelectronic structures or functional features 114 of the patch are not damaged.

The flexible nature of the resulting structure 10 is particularly well suited for attachment to other structures having uneven or flexible surfaces. The resulting structure 10, by way of example, could be affixed to various other objects capable of changing shape without affecting the functioning of the resulting structure 10. Consider, as an example, a sheet of paper or papers or document having the resulting structure 10 attached thereto. The resulting structure 10 may be an RFID tag that can be used to locate the document in a file cabinet, office or other storage facility. Even if the paper or papers of the document are bent or folded, the resulting structure 10 is flexible and can thus continue to function as intended.

As another example, consider a deformable container such as a paper or plastic bag having the resulting structure 10 attached thereto. The plastic bag contain various objects, such as products, biological samples, evidence, etc. The plastic bag may contort or deform to accept objects of various sizes. Since the resulting structure 10 is flexible, it can still perform its intended function, such as location tracking, temperature sensing, etc. even if the container is deformed or changes shape to accept objects of varying sizes.

Consider, as another example, a piece of clothing, a shirt, a pair of underwear, a pair of pants, a shoe, an insole, etc. having resulting structure 10 attached thereto. The clothing may be subjected to stretching, bending, twisting, bodily fluids, sweat, urine, or the like during use. As resulting structure 10 is stretchable, it can still perform its intended function without inhibiting the wearability of the clothing, such as postural measurement, bodily fluid assessment, temperature measurement, light exposure measurement, chemical exposure measurement, ambient condition measurement, stretch measurement, movement, wear-time, washing cycle tracking, wash cycle temperature tracking, usage habits, etc.

For ease of description below, the resulting structure 10 is referred to as patch 10. It should be understood that features described with respect to the patch 10 are not limited solely to a use case wherein the resulting structure 10 is used for physiological monitoring. Instead, various features described below with respect to the patch 10 may be used for other use cases unless specifically noted otherwise.

Figure 14:
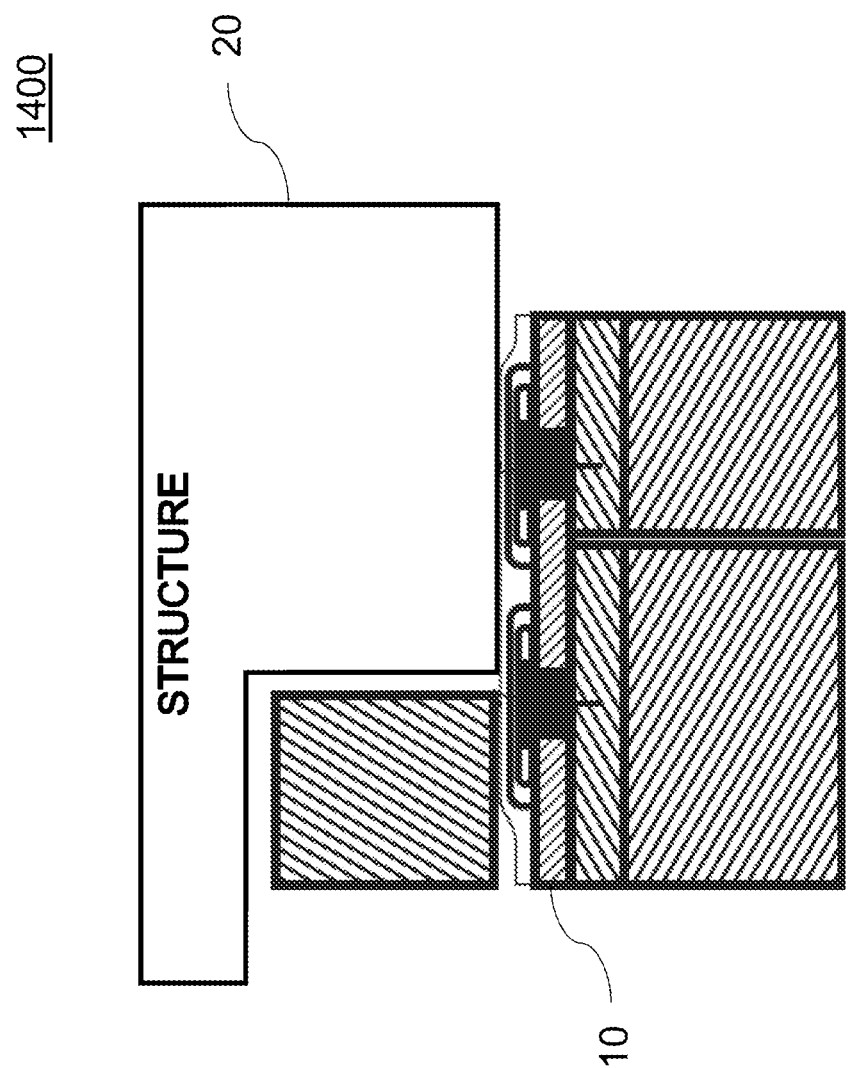
FIG. 14 shows a side cross-sectional view of the thin film support structure of FIG. 13 after removal of a portion of the top carrier and attachment to an additional structure, according to an embodiment of the invention.
Figure 15:
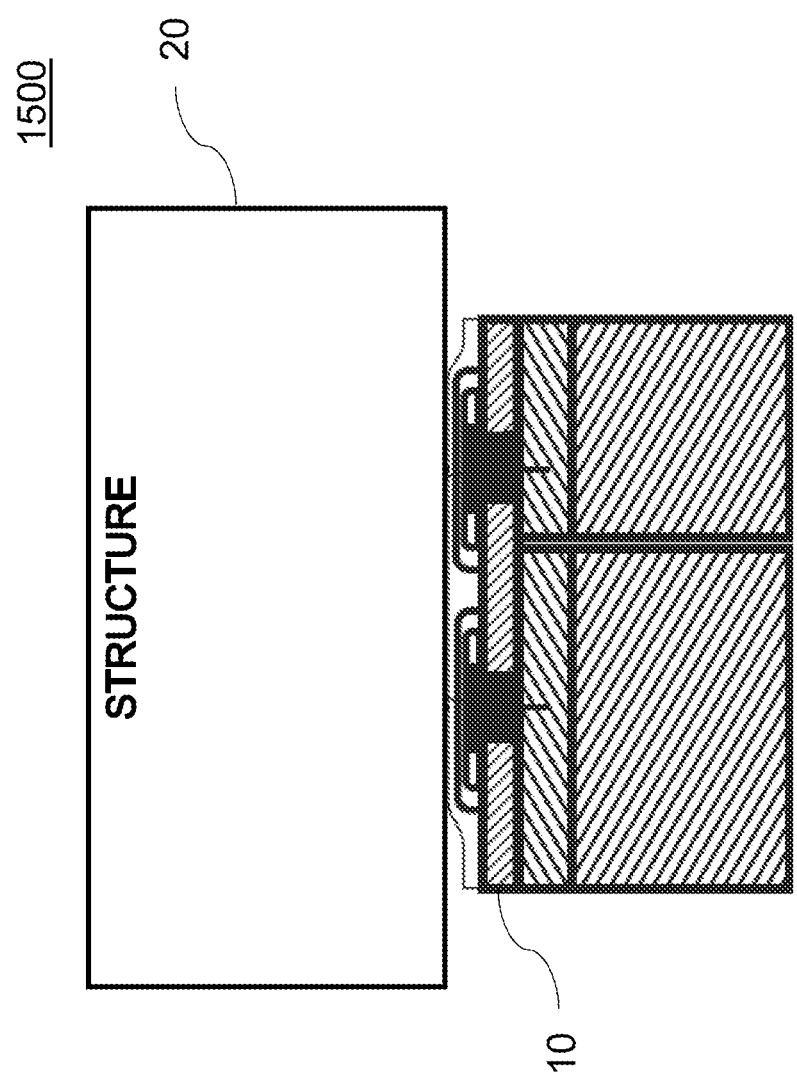
FIG. 15 shows a side cross-sectional view of the FIG. 14 structure after removal of the remainder of the top carrier and attachment to the additional structure, according to an embodiment of the invention.

FIGS. 14-17 depict a process for attaching the patch 10 to a structure 20 and module 30. FIG. 14 shows a side cross-sectional view 1400, where a portion of the top carrier or liner (e.g., 120-2) is removed and the exposed portion is attached to structure 20. One or more of the layers 116 and 118, as well as possibly the functional features 114, may comprise or provide adhesive properties as described above. The structure 20 may be, by way of example, a human body. FIG. 15 shows a side cross-sectional view 1500, where the remaining portion of the top carrier or liner (e.g., 120-1) is removed and the exposed portion is also attached to structure 20. As the film 104 of the patch 10 is generally delicate and easily damageable, removing the top carrier or liner 120 in distinct steps can facilitate simple and reliable attachment of the patch 10 to the structure 20. The patch in a freestanding form (e.g., with the top carrier 120 and bottom carrier 110 removed) may not be able to retain its shape making it more difficult to attach to structure 20. The use of split liners or carriers facilitates the installation of attachment of the patch 10 to the structure 20.

During the attachment procedure illustrated in FIGS. 14-17, the bottom carrier 110 is kept on the patch 10 until the patch 10 is ready to be mated to the module 30. Advantageously, this allows interconnects and functional features 114 of the patch 10 to maintain their precise location facilitating mating of the patch 10 and module 30. In addition, the top carrier 120 as well as the bottom carrier 110 can hermetically seal interconnects and functional features 114 of the patch 10. Once the patch 10 is mated with the structure 20 and module 30, such functional features 114 and interconnects are again hermetically sealed making the system water safe and potentially water submergible during use. As an example, if the patch 10 is used for physiological monitoring, hermetically sealing the functional features 114 and interconnects of the patch 10 to skin of the body 20 and a module 30 allows for use of the patch while a user is in the shower, providing a significant advantage for long-term monitoring.

While FIG. 15 shows an embodiment wherein the entire top side of the patch 10 is attached to structure 10 following removal of the top carrier 120, embodiments are not limited to this arrangement. In some embodiments different portions of the top side of the patch 10 may be affixed to distinct structures. For example, the portion of the top side of the patch 10 exposed by removal of carrier 120-1 may be attached to a first structure while the portion of the top side of the patch 10 exposed by removal of carrier 120-2 may be attached to a second structure. In this manner, different ones of the functional features 114 of the patch 10 may be connected to different structures and used to make measurements or comparison between properties of such different structures. As one example, the top side of patch 10 may be connected to two different biological or other samples and a temperature or other difference between the two may be calculated using different functional features of the patch 10.

Figure 16:
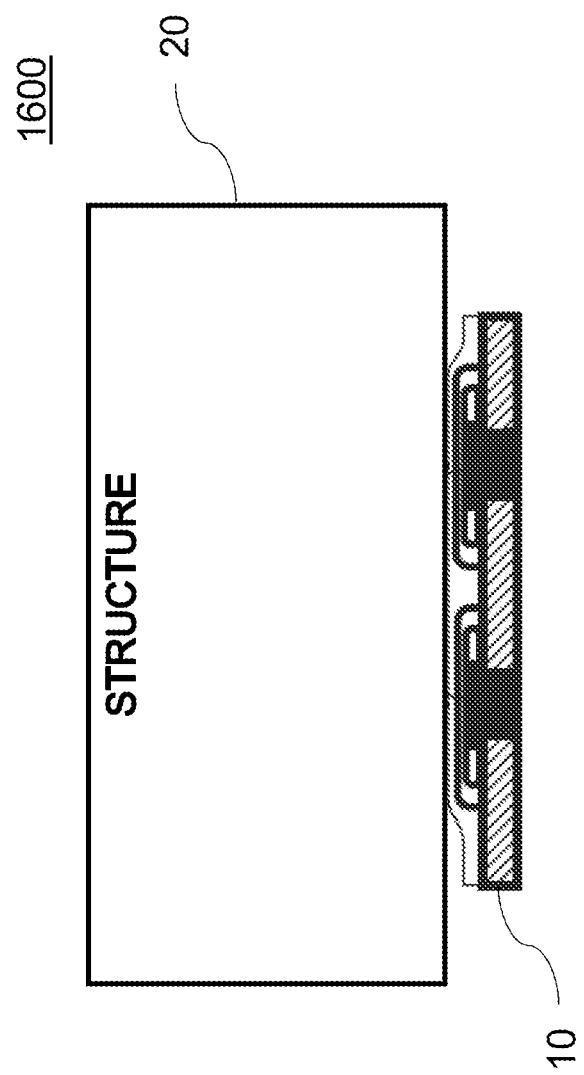
FIG. 16 shows a side cross-sectional view of the FIG. 15 after removal of the bottom carrier, according to an embodiment of the invention.
Figure 17:
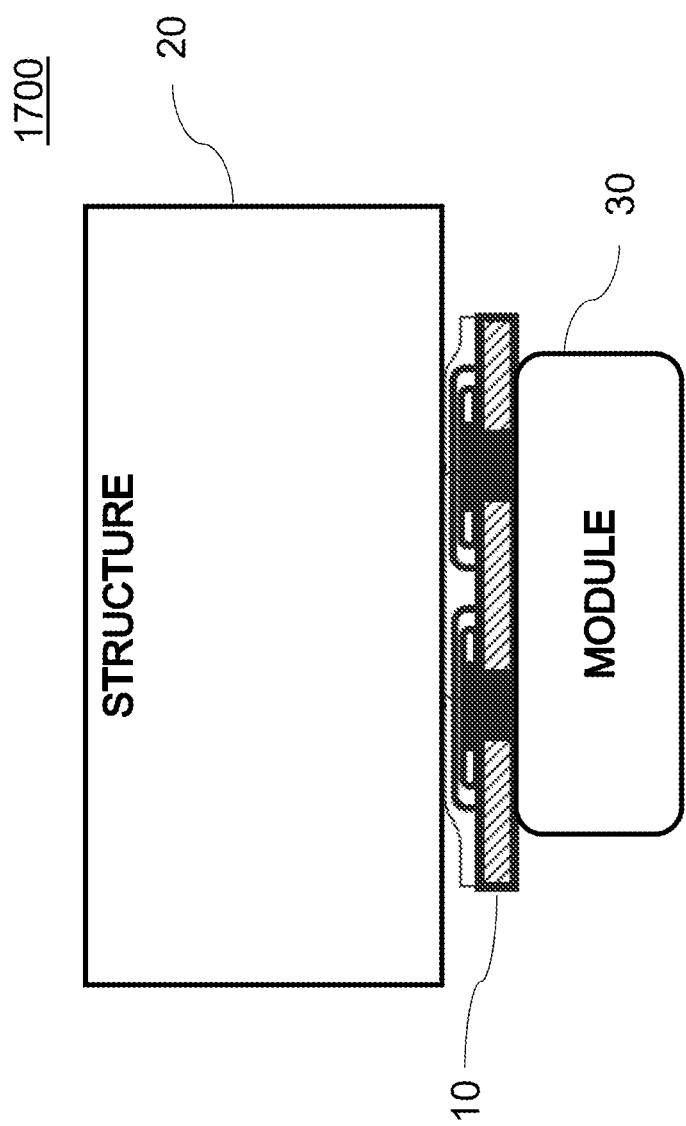
FIG. 17 shows a side cross-sectional view of the FIG. 16 structure attached to a module, according to an embodiment of the invention.

FIG. 16 shows a side cross-sectional view 1600, which shows the patch 10 after removal of the bottom carrier or liner 110. The removal of the bottom carrier 110 may proceed in distinct steps to remove the different portions thereof (e.g., 110-1 may be removed followed by removal of 110-2, or vice versa). FIG. 17 shows a side cross-sectional view 1700, showing attachment of the bottom side of patch 10 to the module 30. The module 30 may provide an adhesive to facilitate this attachment. The patch 10, as described elsewhere herein, may provide an attachment via an intermediate layer such as priming surface 112, functional layers 116 and 118, via functional features 114 of the patch 10 (e.g., magnetic interconnects), one or more gaskets, etc.

FIG. 18 shows a side cross-sectional view 1800, which illustrates one possible manner of interconnection between the patch 10 and module 30. As shown, the patch 10 includes a gasket 1802. The module 30 has mating interconnects 1804 for interfacing with the gasket 1802. In addition to or as an alternative to use of the gasket 1802, the module 30 may have an adhesive or other mechanical interlocking part to secure the module 30 to the patch 10.

FIG. 19 shows a side cross-sectional view 1900 of a structure including film 104, adhesive layer 108 and carrier 110. The view 1900 may be considered as a close-up view of the structure shown in FIGS. 4-9 between functional features 114-1 and 114-2. The FIG. 19 structure also includes a conducting layer 122 formed over a portion of the film 104. The conducting layer 122 may be considered stiff relative to the flexible film 104 after it is cured or dried. The conducting layer 122, in some embodiments is an ink or coating with crosslinking additives. In other embodiments, the conducting layer 122 may be formed of materials including but not limited to a conducting particle filled ink, a conducting polymer, a metal, a patterned metal, etc.

The conducting layer 122, as mentioned above, is formed on a portion of the top side of film 104. The conducting layer 122, in some embodiments, is formed on portions of the top side of the film 104 that are away from through holes 106 formed therein. The conducting layer 122 may, once formed, be used to interconnect different functional features 114 that are formed in the through holes 106 of film 104. The conducting layer 122 may be considered as an example of one of the functional layer 116 and 118 described above.

In some embodiments, the conducting layer 122 is approximately 0.05 µm to 50 µm thick. In other embodiments, the conducting layer 122 may range in thickness from 0.05 µm to 35 µm, from 0.1 µm to 25 µm thick, from 1 to 15 µm thick, or the like. The thickness of the conducting layer 122, however, may vary depending on the needs of a particular use case. In some embodiments, a thin metal layer may be sputter coated, such as though a mask, so as to form a thin conducting layer 122 with a thickness of 0.05 to 1 µm. In other embodiments, a thick film polymer conducting paste may be printed onto the film 104 so as to form a conducting layer 122 with thickness of 1 to 25 µm.

Figure 20:
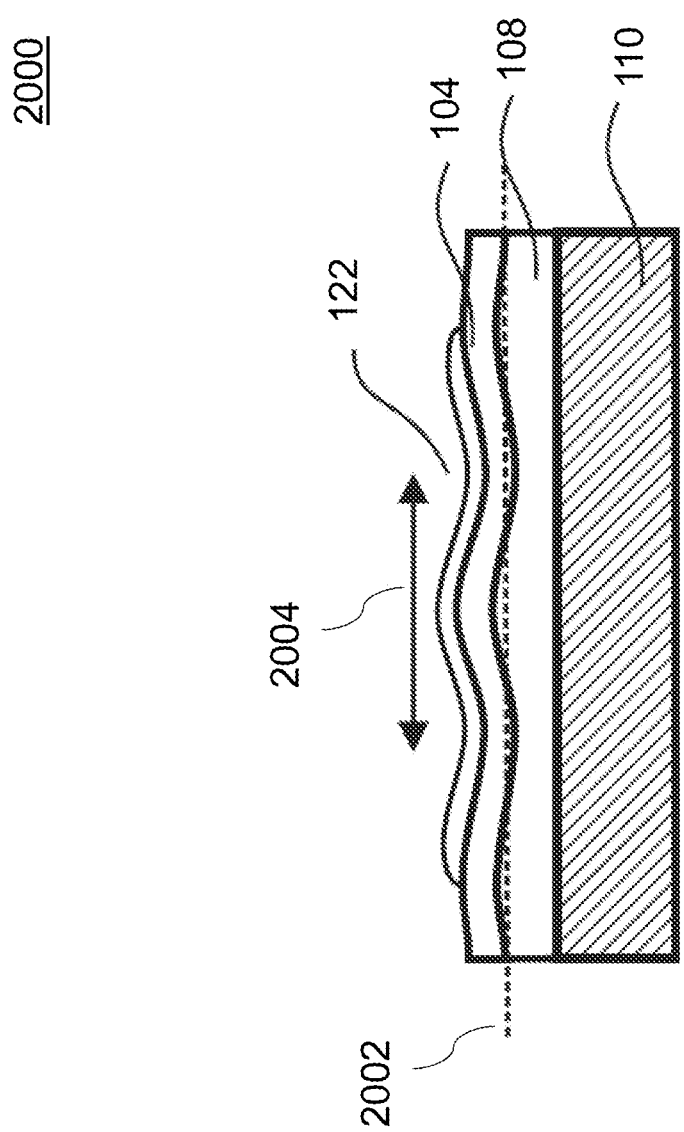
FIG. 20 shows a side cross-sectional view of the FIG. 19 structure after formation of the wrinkle pattern in the conducting layer, according to an embodiment of the invention.

The FIG. 19 structure shows the conducting layer 122 in a pre-cure or as-deposited state. As one example, if the conducting layer 122 is an ink, the FIG. 19 structure may show the ink in wet form. FIG. 20 shows a side cross-sectional view 2000, which illustrates how the FIG. 19 structure changes as the conducting layer 122 cures. It is important to note that the curing process is not limited solely to allowing a wet ink to dry. Various other curing processes may be used, including but not limited to optical cure, oxime cure, room temperature vulcanization, etc. The dashed line 2002 shows the original location of the interface between film 104 and adhesive layer 108 to illustrate the formation of micro- or nano-wrinkles in the FIG. 20 structure. The micro- or nano-wrinkles of the FIG. 20 structure facilitate stretching in the direction illustrated by the double-sided arrow 2004. As illustrated, the micro- or nano-wrinkles are formed with an amplitude oriented substantially in a direction that is perpendicular to the top surface of the film 104 and with a wavelength propagating substantially along a length of the patterned trace formed from the conducting layer 122 with the micro- or nano-wrinkles formed therein.

Figure 21:
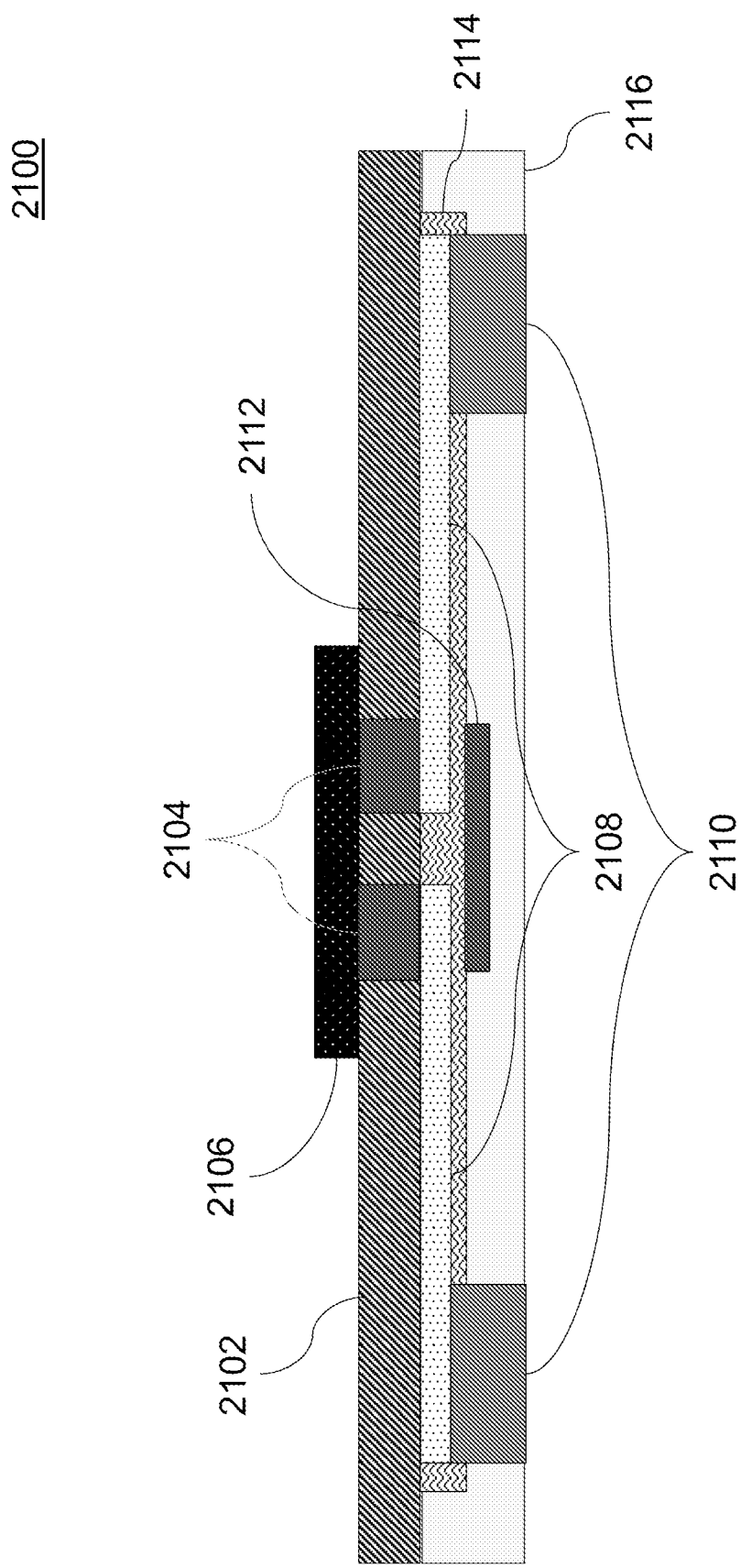
FIG. 21 shows a side cross-sectional view of a thin film structure, according to an embodiment of the invention.

FIG. 21 shows a side cross-sectional view 2100 of a thin film structure. While described below in the context of a patch for medical monitoring, the thin film structure may be used in a variety of other applications, including but not limited to thermal therapeutic devices, such flexible and breathable heating and/or cooling elements with microelectronics or other sensors for feedback, microchannels and microelectronics for drug delivery and/or fluid sensing, temporary tattoos with illumination and/or changing pictures/animations, temporary displays for readouts, touch sensitive elements or panels, interfacial pressure sensing structures, and various other medical applications.

The thin film structure shown in FIG. 21 includes a stack-up of layers, excluding carriers, liners or other support structures described above. The thin film structure includes film 2102 with vias 2104 formed therein. The vias 2104 are shown filled with conductive material. The conductive material may be an electrically conducting material, a thermally conducting material, an electrically and thermally conducting material, etc. A gasket 2106 is formed connected to the vias 2106. Although not explicitly shown, the gasket 2106 may itself have vias formed therein to facilitate mating with a module or other structure similar to that shown and described with respect to FIG. 18.

The thin film structure of FIG. 21 also includes conductive traces 2108 that connect the conductive material formed in vias 2104 with ionically and/or intrinsically conducting regions 2110. The regions 2110 may, for example, be body electrodes. The thin film structure further includes magnetic material 2112 separated from the conductive traces 2108 insulation 2114. Adhesive 2116 is shown surrounding the bottom surface of the structure to facilitate attachment to a structure such as the skin of a subject. The magnetic material 2112 may be ferromagnetic material that facilitates placements and/or attachment of the gasket 2106 to a monitoring module such as module 30 described above. While not explicitly shown, split liners and/or carriers may be formed on a top and/or bottom of the thin film structure to facilitate attachment to a module and/or body.

The thin film structure or patch of FIG. 21 may be configured to attachment to module 30 via the gasket 2106 as described above. The module 30 may include a battery or other power source, and may be used to provide power to one or more microelectronic structures of the patch, either directly or through conductive material in vias formed therein and possible one or more conducting traces. The module 30 may also be configured with signal conditioning circuitry, signal processing circuitry, a processor, a volatile or non-volatile memory, a radio, and/or the like used to record signals that are obtained using the patch.

As mentioned above, FIGS. 1-21 are not necessarily drawn to scale solely for ease of illustration. The patch 10, with liner(s) in place, as an example, may be less than 0.25 mm thick, less than 0.150 mm, less than 0.075 mm thick, less than 0.05 mm thick, or the like. In some embodiments, the patch 10 may be as thin as 0.0125 mm. The patch 10 may thus be extremely thin but also elastomeric. The techniques described herein permit formation and handling of such extremely thin and elastomeric films including attachment to other structures. The particular thickness of the patch 10 may be chosen or selected based on a use case scenario, or the space needed for forming functional features 114 of the patch 10. Thus, in some cases the patch 10 may be thinner than 0.025 mm. After liner removal, the thickness of patch 10 may be less than 0.03 mm thick, less than 0.025 mm thick, less than 0.02 mm thick, or less than 0.012 mm thick. It is important to note, however, that the thickness of the patch 10, before or after removal of the liners, is not necessarily uniform. As shown, the functional features 114 of patch 10 span from a first surface (i.e., the bottom side in the figures also referred to as the device-side or module-side) of the patch 10 to a second surface (e.g., the top side in the figures also referred to as the body-side) of the patch 10. The functional features 114 also protrude at least partially above the top side of the patch 10 in the specific examples shown, although this is not a requirement.

In one embodiment, a method comprises forming a film, forming a first pattern of two or more vias at least partially through the film, attaching the film to a first support structure, the first support structure comprising an adhesive layer formed over a first carrier, wherein attaching the film to the first support structure comprises bonding a first surface of the film to the adhesive layer of the first support structure, wherein the film is stretchable in at least a first direction along the first surface, and wherein the first carrier maintains the first pattern of vias within a given threshold distortion following a given process conducted after attaching the film to the first support structure.

In some embodiments, the given threshold distortion comprises distortion less than 1%, less than 0.25%, less than 0.1%, or less than 0.01%. The given threshold distortion may be distortion less than 10 micrometers (μm), less than 5 μm, or less than 1 μm. The given threshold distortion may be distortion in distance between centers of adjacent ones of the vias less than 10 μm, less than 5 μm, or less than 1 μm.

In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin, and the first carrier comprises one or more of biaxially-oriented polyethylene terephthalate (BoPET), polyethylene naphthalate (PEN), biaxially-oriented PEN (BoPEN), polyethylene terephthalate (PET), polycarbonate (PC)/acrylonitrile butadiene styrene (ABS), PC/acrylonitrile styrene (AS), polybutylene naphthalate (PBN), polyimide (PI), and polyphenylene sulfide (PPS).

In some embodiments, an elastic modulus of the first carrier is at least five times greater than an elastic modulus of the film, at least ten times greater than an elastic modulus of the film, at least fifty times greater than an elastic modulus of the film, at least one hundred times greater than an elastic modulus of the film, or at least five hundred times greater than an elastic modulus of the film.

In some embodiments, the given process comprises heating to a temperature greater than 100 degrees Celsius (° C.), greater than 120° C., greater than 140° C., greater than 160° C., or greater than 180° C. for at least one minute subsequent to attaching the film to the first support structure, for at least two minutes subsequent to attaching the film to the first support structure, for at least five minutes subsequent to attaching the film to the first support structure, or for at least ten minutes subsequent to attaching the film to the first support structure.

In some embodiments, the given process comprises cooling to a temperature less than 5° C., less than 0° C., less than −10° C., or less than −15° C. for at least five seconds subsequent to attaching the film to the first support structure, for at least thirty seconds subsequent to attaching the film to the first support structure, for at least one minute subsequent to attaching the film to the first support structure, or for at least two minutes subsequent to attaching the film to the first support structure.

In some embodiments, the method further comprises forming one or more microelectronic structures registered to one or more of the vias, the registration being within 1 millimeters (mm) of a preferred positioning, within 0.5 mm of a preferred positioning, within 0.25 mm of a preferred positioning, within 0.1 mm of a preferred positioning, within 0.05 mm of a preferred positioning, or within 0.025 mm of a preferred positioning.

In some embodiments, the method further comprises exposing the film to a chemical that at least partially solvates the film.

In some embodiments, the given process comprises pulling the film along a web after attaching the film to the first support structure or roll-to-roll or web based processing of the film after attaching the film to the first support structure.

In some embodiments, the method further comprises at least partially filling one or more of the vias with an electrically conducting material, with a thermally conducting material, or with an electrically and thermally conducting material.

In some embodiments, forming the film further comprises bonding a second surface of the film to a second carrier to form a second support structure, the second surface of the film being opposite the first surface of the film and attaching the film to the support structure comprises attaching the second support structure to the first support structure and removing the second carrier. In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin, and the second carrier comprises one or more of biaxially oriented polypropylene (BOPP), casting paper, polycarbonate, polyethylene, a print receptive substrate, a siliconized liner, a polyester liner, and a web-supporting material.

In some embodiments, the film has a thickness of 0.0025 to 1.0 mm.

In some embodiments, the film comprises a stretchable and breathable material. In some embodiments, the film comprises a stretchable, breathable, and elastically recoverable material.

In some embodiments, the method further comprises forming at least one split in the first carrier prior to attaching the film to the first support structure.

In some embodiments, the method further comprises curing or drying the adhesive layer prior to attaching the film to the first support structure. In some embodiments, the adhesive layer comprises one or more of a low tack gel adhesive, a crosslinked gel polymer, a pressure sensitive adhesive, and a low tack adhesive. In some embodiments, the adhesive layer comprises a friction lowering substance such that a thin residue remains on the film after removing the first support structure from the film, the friction lowering substance comprising one or more of a polymer resin, an oil, an excipient, a blooming agent, a silicone oil, and a wax.

In some embodiments, the method further comprises forming at least one functional feature over a second surface of the film, the second surface of the film being opposite the first surface of the film. In some embodiments, forming the at least one functional feature comprises forming the at least one functional feature aligned with at least one of the vias.

In some embodiments, forming the at least one functional feature comprises forming the at least one functional feature registered to at least one of the vias. In some embodiments, the at least one functional feature comprises a gasket facilitating attachment of the film to another structure, the gasket being formed prior to attaching the film to the first support structure. In some embodiments, the at least one functional feature comprises an electrical feature, a capacitive element, a resistive element, a touch sensitive component, a flexible display element, a pixel, an analyte sensing element, a printed electrochemical sensor, a touch sensitive element, or a light sensitive element.

In some embodiments, attaching the film to the first support structure comprises laminating the first surface of the film to the adhesive layer.

In some embodiments, at least one of the vias is formed completely through the film. In some embodiments, the method further comprises depositing an additional material on regions of the adhesive layer exposed by the at least one via formed completely through the film. In some embodiments, the additional material comprises a conductive material. In some embodiments, the conductive material comprises an electrically conductive material, a thermally conductive material, or an electrically and thermally conductive material. In some embodiments, the conductive material adheres more strongly to the film than to the adhesive layer. In some embodiments, the conductive material comprises an adhesive strength to the adhesive layer of less than 75 grams per inch (g/in), of less than 50 g/in, of less than 25 g/in, or of less than 10 g/in. In some embodiments, the additional material comprises a release coating. In some embodiments, the release coating comprises one or more of a siliconized release coating, a mold release medium, and a wax. In some embodiments, the additional material comprises a release coating and a conductive material formed over the release coating. In some embodiments, the conductive material adheres more strongly to the film than to the release coating. In some embodiments, the conductive material comprises an adhesive strength to the release coating of less than 75 g/in, of less than 50 g/in, of less than 25 g/in, or of less than 10 g/in.

In some embodiments, the method further comprises forming a priming surface over at least a portion of a second surface of the film, the second surface of the film being opposite the first surface of the film. In some embodiments, the priming surface comprises one or more of an organometallic self-assembled monolayer, a titanate, a zirconate, an aluminate, an organosilane, a silane, and a siloxane.

In some embodiments, the method further comprises forming at least one functional feature in at least one of the vias. In some embodiments, the at least one functional feature comprises a microelectronic structure comprising one or more layers. In some embodiments, at least one of the layers of the microelectronic structure has a thickness less than 50 μm. In some embodiments, the microelectronic structure has an equivalent bulk elastic modulus of less than 900 megapascals (MPa). In some embodiments, the microelectronic structure has an equivalent flexural modulus of less than 1 gigapascal (GPa). In some embodiments, a moisture vapor transfer rate (MVTR) in an area of the film proximate the microelectronic structure is greater than 50 grams per square meter per day (g/m$^2$/day).

In some embodiments, the method further comprises forming a first functional feature in a first one of the vias and forming at least a first functional layer over a second surface of the film opposite the first surface of the film, the first functional layer connecting to the first functional feature. In some embodiments, the method further comprises forming a second functional feature in a second one of the vias, the first functional layer connecting the first functional feature to the second functional feature. In some embodiments, the first functional layer comprises a patterned trace. In some embodiments, forming the first functional layer comprises depositing a conducting layer over a first portion of the second surface of the film and at least one of curing and drying the conducting layer to form one or more wrinkles therein, the conducting layer with wrinkles formed therein forming the patterned trace. In some embodiments, the wrinkles are formed with an amplitude oriented substantially in a direction perpendicular to the second surface of the film. In some embodiments, the wrinkles are formed with a wavelength propagating substantially along a length of the patterned trace. In some embodiments, the first functional feature comprises an electrical interconnect, a light emitting pixel, a flexible display, a light emitting temporary tattoo, a light emitting diode (LED), a flexible LED, an electrode, a reference electrode, an electrochemical sensor, a redox reactive sensing electrode, a light sensitive structure, a moisture sensitive structure, a pressure sensitive structure, or a magnetic structure.

In one embodiment, an apparatus comprises a first support structure comprising an adhesive layer formed over a first carrier and a film attached to the first support structure and comprising a first pattern of two or more vias formed at least partially therethrough, a first surface of the film being bonded to the adhesive layer of the first support structure, wherein the film is stretchable in at least a first direction along the first surface and wherein the first carrier comprises a material having a rigidity that maintains the first pattern of vias within a given threshold distortion following a given process conducted after the film is attached to the first support structure.

In some embodiments, the given threshold distortion comprises distortion less than 1%, less than 0.25%, less than 0.1%, or less than 0.01%. The given threshold distortion may be distortion less than 10 µm, less than 5 µm, or less than 1 µm. The given threshold distortion may be distortion in distance between centers of adjacent ones of the vias less than 10 µm, less than 5 µm, or less than 1 µm.

In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin, and the first carrier comprises one or more of biaxially-oriented polyethylene terephthalate (BoPET), polyethylene naphthalate (PEN), biaxially-oriented PEN (BoPEN), polyethylene terephthalate (PET), polycarbonate (PC)/acrylonitrile butadiene styrene (ABS), PC/acrylonitrile styrene (AS), polybutylene naphthalate (PBN), polyimide (PI), and polyphenylene sulfide (PPS).

In some embodiments, an elastic modulus of the first carrier is at least five times greater than an elastic modulus of the film, at least ten times greater than an elastic modulus of the film, at least fifty times greater than an elastic modulus of the film, at least one hundred times greater than an elastic modulus of the film, or at least five hundred times greater than an elastic modulus of the film.

In some embodiments, the given process comprises heating to a temperature greater than 100 degrees Celsius (° C.), greater than 120° C., greater than 140° C., greater than 160° C., or greater than 180° C. for at least one minute subsequent to attaching the film to the first support structure, for at least two minutes subsequent to attaching the film to the first support structure, for at least five minutes subsequent to attaching the film to the first support structure, or for at least ten minutes subsequent to attaching the film to the first support structure.

In some embodiments, the given process comprises cooling to a temperature less than 5° C., less than 0° C., less than −10° C., or less than −15° C. for at least five seconds subsequent to attaching the film to the first support structure, for at least thirty seconds subsequent to attaching the film to the first support structure, for at least one minute subsequent to attaching the film to the first support structure, or for at least two minutes subsequent to attaching the film to the first support structure.

In some embodiments, the apparatus further comprises one or more microelectronic structures registered to one or more of the vias, the registration being within 1 mm of a preferred positioning, within 0.5 mm of a preferred positioning, within 0.25 mm of a preferred positioning, within 0.1 mm of a preferred positioning, within 0.05 mm of a preferred positioning, or within 0.025 mm of a preferred positioning.

In some embodiments, the film is at least partially solvated by exposure to a chemical.

In some embodiments, the given process comprises pulling the film along a web after attaching the film to the first support structure or roll-to-roll or web based processing of the film after attaching the film to the first support structure.

In some embodiments, the apparatus further comprises an electrically conducting material at least partially filling one or more of the vias, a thermally conducting material at least partially filling one or more of the vias, or an electrically and thermally conducting material at least partially filling one or more of the vias.

In some embodiments, the film is part of a second support structure, the second support structure comprising a second carrier bonded to a second surface of the film, the second surface of the film being opposite the first surface of the film. In some embodiments, the film comprises one or more of polyurethane (PU), an elastomer, a silicone rubber, a silicone gel, a fluorosilicone rubber, a fluoroelastomer, a perfluoroelastomer, a polyether block amide, an ethylene-vinyl acetate, a polybutadiene, BR, a natural or synthetic polyisoprene, a copolyester, neoprene, natural rubber, ethylene propylene diene terpolymer (EPDM), styrene-butadiene rubber (SBR), nitrile, a thermoplastic elastomer, a styrenic block copolymer, a thermoplastic olefin, a polyamide, a cross-linked protein, elastin, and a resilin and the second carrier comprises one or more of biaxially oriented polypropylene (BOPP), casting paper, a print receptive substrate, a siliconized liner, a polyester liner, and a web-supporting material.

In some embodiments, the film has a thickness of 0.0025 to 1.0 mm.

In some embodiments, the film comprises a stretchable and breathable material. In some embodiments, the film comprises a stretchable, breathable, and elastically recoverable material.

In some embodiments, the first carrier has at least one split formed therein.

In some embodiments, the adhesive layer is dried or cured prior to attachment of the film to the first support structure.

In some embodiments, the adhesive layer comprises one or more of a low tack gel adhesive, a crosslinked gel polymer, a pressure sensitive adhesive, and a low tack adhesive. In some embodiments, the adhesive layer comprises a friction lowering substance such that a thin residue remains on the film after removing the first support structure from the film, the friction lowering substance comprising one or more of a polymer resin, an oil, an excipient, a blooming agent, a silicone oil, and a wax.

In some embodiments, the apparatus further comprises at least one functional feature formed over a second surface of the film, the second surface of the film being opposite the first surface of the film. In some embodiments, the at least one functional feature is aligned with at least one of the vias. In some embodiments, the at least one functional feature is registered to at least one of the vias. In some embodiments, the at least one functional feature comprises a gasket facilitating attachment of the film to another structure. In some embodiments, the at least one functional feature comprises an electrical feature, a capacitive element, a resistive element, a touch sensitive component, a flexible display element, a pixel, an analyte sensing element, a printed electrochemical sensor, a touch sensitive element, or a light sensitive element.

In some embodiments, the first surface of the film is laminated to the adhesive layer. In some embodiments, at least one of the vias is formed completely through the film. In some embodiments, the apparatus further comprises an additional material deposited on regions of the adhesive layer exposed by the at least one via formed completely through the film. In some embodiments, the additional material comprises a conductive material. In some embodiments, the conductive material comprises an electrically conductive material, a thermally conductive material, or an electrically and thermally conductive material. In some embodiments, the conductive material adheres more strongly to the film than to the adhesive layer. In some embodiments, the conductive material comprises an adhesive strength to the adhesive layer of less than 75 g/in, less than 50 g/in, less than 25 g/in, or less than 10 g/in. In some embodiments, the additional material comprises a release coating. In some embodiments, the release coating comprises one or more of a siliconized release coating, a mold release medium, and a wax. In some embodiments, the additional material comprises a release coating and a conductive material formed over the release coating. In some embodiments, the conductive material adheres more strongly to the film than to the release coating. In some embodiments, the conductive material comprises an adhesive strength to the release coating of less than 75 g/in, less than 50 g/in, less than 25 g/in, or less than 10 g/in.

In some embodiments, the apparatus further comprises a priming surface formed over at least a portion of a second surface of the film, the second surface of the film being opposite the first surface of the film. In some embodiments, the priming surface comprises one or more of an organometallic self-assembled monolayer, a titanate, a zirconate, an aluminate, an organosilane, a silane, and a siloxane.

In some embodiments, the apparatus further comprises at least one functional feature formed in at least one of the vias. In some embodiments, the at least one functional feature comprises a microelectronic structure comprising one or more layers. In some embodiments, at least one of the layers of the microelectronic structure has a thickness less than 50 µm. In some embodiments, the microelectronic structure has an equivalent bulk elastic modulus of less than 900 megapascals (MPa). In some embodiments, the microelectronic structure has an equivalent flexural modulus of less than 1 gigapascal (GPa). In some embodiments, a moisture vapor transfer rate (MVTR) in an area of the film proximate the microelectronic structure is greater than 50 grams per square meter per day (g/m$^2$/day).

In some embodiments, the apparatus further comprises a first functional feature formed in a first one of the vias and at least a first functional layer formed over a second surface of the film opposite the first surface of the film, the first functional layer connecting to the first functional feature. In some embodiments, the apparatus further comprises a second functional feature formed in a second one of the vias, the first functional layer connecting the first functional feature to the second functional feature. In some embodiments, the first functional layer comprises a patterned trace. In some embodiments, the patterned trace comprises a conducting layer that is at least one of cured and dried to form one or more wrinkles therein. In some embodiments, the wrinkles are formed with an amplitude oriented substantially in a direction perpendicular to the second surface of the film. In some embodiments, the wrinkles are formed with a wavelength propagating substantially along a length of the patterned trace. In some embodiments, the first functional feature comprises an electrical interconnect, a light emitting pixel, a flexible display, a light emitting temporary tattoo, a light emitting diode (LED), a flexible LED, an electrode, a reference electrode, an electrochemical sensor, a redox reactive sensing electrode, a light sensitive structure, a moisture sensitive structure, a pressure sensitive structure, or a magnetic structure.

In one embodiment, a patch comprises a first support structure comprising an adhesive layer formed over a first carrier, a film attached to the first support structure and comprising a first pattern of two or more vias formed at least partially therethrough, a first surface of the film being bonded to the adhesive layer of the first support structure, one or more microelectronic structures, the one or more microelectronic structures being at least one of: formed in at least one of the vias; and formed as a pattern on a second surface of the film, the second surface of the film being opposite the first surface of the film, a surface adhesive formed over at least a portion of the second surface of the film, and a liner attached to the surface adhesive, wherein the film is stretchable in at least a first direction along the first surface and wherein the first carrier comprises a material having a rigidity that maintains the first pattern of vias within a given threshold distortion following a given process conducted after the film is attached to the first support structure.

In some embodiments, the patch further comprises a module coupled to at least one of: the one or more microelectronic structures; and one or more of the vias. In some embodiments, the module provides power to at least a given one of the microelectronic structures. In some embodiments, the module provides power to the given microelectronic structures through at least a given one of the vias. In some embodiments, the module is configured to record a signal obtained using one or more of the microelectronic structures. In some embodiments, the patch further comprises a gasket formed on the first surface of the film, the gasket facilitating coupling of the module to the one or more microelectronic structures and the one or more vias.

In some embodiments, the patch further comprises at least one conductive trace connecting a first microelectronic structure formed on the second surface of the film with conductive material in a first one of the vias. In some embodiments, the first microelectronic structure comprises a body electrode.

In one embodiment, a method comprises providing a patch, the patch comprising a first support structure comprising an adhesive layer formed over a first carrier, a film attached to the first support structure and comprising a first pattern of two or more vias formed at least partially therethrough, a first surface of the film being bonded to the adhesive layer of the first support structure, one or more microelectronic structures, the one or more microelectronic structures being at least one of: formed in at least one of the vias; and formed as a pattern on a second surface of the film, the second surface of the film being opposite the first surface of the film, a surface adhesive formed over at least a portion of the second surface of the film, and a liner attached to the surface adhesive, wherein the film is stretchable in at least a first direction along the first surface and wherein the first carrier comprises a material having a rigidity that maintains the first pattern of vias within a given threshold distortion following a given process conducted after the film is attached to the first support structure. The method further comprises removing at least a portion of the liner to expose at least a first region of the surface adhesive, attaching the patch to a first structure by bonding the exposed first region of the surface adhesive to a first surface of the first structure, and removing at least a portion of the first carrier.

In some embodiments, the method further comprises removing a remaining portion of the liner after attaching the patch to the first structure to expose at least a second region of the surface adhesive and bonding the exposed second region of the surface adhesive to the first surface of the first structure.

In some embodiments, the method further comprises removing a remaining portion of the liner after attaching the patch to the first structure to expose at least a second region of the surface adhesive and bonding the exposed second region of the surface adhesive to a second surface of the first structure.

In some embodiments, the method further comprises removing a remaining portion of the liner after attaching the patch to the first structure to expose at least a second region of the surface adhesive and bonding the exposed second region of the surface adhesive to a first surface of a second structure.

In some embodiments, the first structure comprises skin of a subject, a container, or a product.

In some embodiments, the method further comprises providing a module and attaching the module to the patch to couple the module with at least one of: one or more of the microelectronic structures; and one or more of the vias. In some embodiments, the method further comprises providing power to one or more of the microelectronic structures from the module. In some embodiments, providing power to one or more of the microelectronic structures from the module comprises providing power to the microelectronic structures through at least one of the vias. In some embodiments, the method further comprises utilizing the module to record at least one signal obtained from the first structure using the one or more microelectronic structures.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. An apparatus comprising:
 a first support structure comprising an adhesive layer formed over a first carrier;
 a film attached to the first support structure and comprising a first pattern of two or more vias formed at least partially therethrough, a first surface of the film being bonded to the adhesive layer of the first support structure;
 wherein the film is stretchable in at least a first direction along the first surface; and
 at least one functional layer formed over a second surface of the film opposite the first surface of the film, the at least one functional layer comprising one or more wrinkles, the one or more wrinkles having (i) an amplitude oriented substantially in a direction perpendicular to the second surface of the film and (ii) a wavelength propagating substantially along the first direction along the first surface, the one or more wrinkles enabling stretching of the at least one functional layer in the first direction along the first surface;
 wherein the first carrier comprises a material having a first rigidity greater than a second rigidity of the film, the first carrier maintaining the first pattern of vias within a given threshold distortion following a given process conducted after the film is attached to the first support structure, the given threshold distortion being at least one of distortion less than 1% in locations of the two or more vias in the pattern of vias before and after the given process, distortion less than 10 micrometers ($\mu$m) in the first direction, and distortion in distance between centers of adjacent ones of the vias less than 10 $\mu$m.

2. The apparatus of claim 1, wherein the given threshold distortion comprises at least one of distortion less than 0.25% in locations of the two or more vias in the pattern of vias before and after the given process, distortion less than 5 $\mu$m in the first direction, and distortion in distance between centers of adjacent ones of the vias less than 5 $\mu$m.

3. The apparatus of claim 1, further comprising one or more microelectronic structures aligned to one or more of the vias, the alignment being within 1 mm of a preferred positioning.

4. The apparatus of claim 1, further comprising at least one functional feature formed over a second surface of the film, the second surface of the film being opposite the first surface of the film, the at least one functional feature being aligned with at least one of the vias.

5. The apparatus of claim 4, wherein the at least one functional feature comprises a gasket facilitating attachment of the film to another structure.

6. The apparatus of claim 1, wherein at least one of the vias is formed completely through the film, and further comprising an additional material deposited on regions of the adhesive layer exposed by the at least one via formed completely through the film, the additional material comprising at least one of an electrically conductive material and a thermally conductive material.

7. The apparatus of claim 1, wherein at least one of the vias is formed completely through the film, and further comprising an additional material deposited on regions of the adhesive layer exposed by the at least one via formed completely through the film, the additional material comprising a release coating, the release coating comprises one or more of a siliconized release coating, a mold release medium, and a wax.

8. The apparatus of claim 7, wherein the additional material further comprises a conductive material formed over the release coating, the conductive material adhering more strongly to the film than to the release coating.

9. The apparatus of claim 1, further comprising at least one functional feature formed in at least one of the vias, the at least one functional feature comprising a microelectronic structure comprising one or more layers, at least one of the layers of the microelectronic structure having a thickness less than 50 μm.

10. The apparatus of claim 9, wherein at least one of:
the microelectronic structure has an equivalent bulk elastic modulus of less than 900 megapascals (MPa);
the microelectronic structure has an equivalent flexural modulus of less than 1 gigapascal (GPa); and
a moisture vapor transfer rate (MVTR) in an area of the film proximate the microelectronic structure is greater than 50 grams per square meter per day (g/m²/day).

11. The apparatus of claim 1, further comprising:
a first functional feature formed in a first one of the vias; and
a second functional feature formed in a second one of the vias;
wherein the at least one functional layer comprises a first functional layer connecting the first functional feature to the second functional feature.

12. The apparatus of claim 11, wherein the first functional layer comprises a patterned trace, the patterned trace comprises a conducting layer that is at least one of cured and dried to form the one or more wrinkles.

13. A patch comprising:
a first support structure comprising an adhesive layer formed over a first carrier;
a film attached to the first support structure and comprising a first pattern of two or more vias formed at least partially therethrough, a first surface of the film being bonded to the adhesive layer of the first support structure;
one or more microelectronic structures, the one or more microelectronic structures being at least one of formed in at least one of the vias, and formed as a pattern on a second surface of the film, the second surface of the film being opposite the first surface of the film;
a surface adhesive formed over at least a portion of the second surface of the film;
a liner attached to the surface adhesive;
wherein the film is stretchable in at least a first direction along the first surface; and
at least one functional layer formed over the second surface of the film, the at least one functional layer comprising one or more wrinkles, the one or more wrinkles having (i) an amplitude oriented substantially in a direction perpendicular to the second surface of the film and (ii) a wavelength propagating substantially along the first direction along the first surface the one or more wrinkles enabling stretching of the at least one functional layer in the first direction along the first surface;
wherein the first carrier comprises a material having a first rigidity greater than a second rigidity of the film, the first carrier maintaining the first pattern of vias within a given threshold distortion following a given process conducted after the film is attached to the first support structure, the given threshold distortion being at least one of distortion less than 1% in locations of the two or more vias in the pattern of vias before and after the given process, distortion less than 10 micrometers (μm) in the first direction, and distortion in distance between centers of adjacent ones of the vias less than 10 μm.

14. The patch of claim 13, further comprising:
a module coupled to at least one of the one or more microelectronic structures, and one or more of the vias;
wherein the module is configured to at least one of provide power to at least a given one of the microelectronic structures through at least a given one of the vias, and record a signal obtained using one or more of the microelectronic structures.

15. The patch of claim 14, further comprising a gasket, the gasket facilitating coupling of the module to the one or more microelectronic structures and the one or more vias.

16. The patch of claim 13, wherein the at least one functional layer comprises at least one conductive trace connecting a first microelectronic structure formed on the second surface of the film with conductive material in a first one of the vias.

17. The apparatus of claim 1 wherein the given process comprises forming at least one microelectronic structure in at least one of the vias, wherein forming the at least one microelectronic structure in the at least one via exposes the film to at least one of a solvent that causes a material of the film to distort, a temperature that causes the material of the film to melt, and tension that causes the material of the film to stretch in the first direction.

18. The patch of claim 13 wherein the given process comprises forming the one or more microelectronic structures, wherein forming the one or more microelectronic structures exposes the film to at least one of a solvent that causes a material of the film to distort, a temperature that causes the material of the film to melt, and tension that causes the material of the film to stretch in the first direction.

19. The apparatus of claim 1, wherein the at least one functional layer comprises a conductive ink with one or more crosslinking additives.

20. The apparatus of claim 1, wherein the at least one functional layer comprises a conducting particle filled ink.

* * * * *